United States Patent
Li et al.

(10) Patent No.: US 9,926,604 B2
(45) Date of Patent: Mar. 27, 2018

(54) MULTIPLEX PCR-BASED TESTING OF CUTANEOUS SQUAMOUS CELL CARCINOMA AND PSEUDOEPITHELIOMATOUS HYPERPLASIA AND METHODS FOR DISTINGUISHING THE SAME

(71) Applicant: The Regents of the University of California, Oakland, CA (US)

(72) Inventors: XinMin Li, Tarzana, CA (US); Jian Zhou, Agoura Hills, CA (US); Scott W. Binder, Beverly Hills, CA (US); Seong Ra, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 605 days.

(21) Appl. No.: 14/351,694

(22) PCT Filed: Oct. 12, 2012

(86) PCT No.: PCT/US2012/059947
§ 371 (c)(1),
(2) Date: Apr. 14, 2014

(87) PCT Pub. No.: WO2013/056042
PCT Pub. Date: Apr. 18, 2013

(65) Prior Publication Data
US 2014/0242598 A1 Aug. 28, 2014

Related U.S. Application Data

(60) Provisional application No. 61/547,272, filed on Oct. 14, 2011.

(51) Int. Cl.
*C12Q 1/68* (2006.01)

(52) U.S. Cl.
CPC ...... *C12Q 1/6886* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 2006/0024692 A1 | 2/2006 | Nakamura et al. |
| 2007/0105133 A1 | 5/2007 | Clarke et al. |
| 2009/0170132 A1* | 7/2009 | Pevsner ............... G01N 33/574 435/7.23 |

FOREIGN PATENT DOCUMENTS

| | | |
|---|---|---|
| CN | 1355174 A | 6/2002 |
| CN | 1381476 A | 11/2002 |
| EP | 2 278 028 A1 | 1/2011 |
| EP | 2 392 675 A1 | 12/2011 |
| WO | WO 2004/042000 A2 | 5/2004 |

OTHER PUBLICATIONS

Lambert, Sally Ruth. Molecular profiling of cutaneous squamous cell carcinoma. PhD diss., 2010.*
Lowe T, Sharefkin J, Yang SQ, Dieffenbach CW. A computer program for selection of oligonucleotide primers for polymerase chain reactions. Nucleic Acids Res. Apr. 11, 1990; 18(7):1757-61.*
Ra SH, Li X, Binder S. Molecular discrimination of cutaneous squamous cell carcinoma from actinic keratosis and normal skin. Mod Pathol. Jul. 2011; 24(7):963-73.*
Visser M, Zubakov D, Ballantyne KN, Kayser M. mRNA-based skin identification for forensic applications. Int J Legal Med. Mar. 2011; 125(2):253-63.*
Zhou J, Wang H, Lu A, Hu G, Luo A, Ding F, Zhang J, Wang X, Wu M, Liu Z. A novel gene, NMES1, downregulated in human esophageal squamous cell carcinoma. Int J Cancer. Oct. 1, 2002; 101(4):311-6.*
Haider et al., "Genomic Analysis Defines a Cancer-Specific Gene Expression Signature for Human Squamous Cell Carcinoma and Distinguishes Malignant Hyperproliferation from Benign Hyperplasia," *The Society for Investigative Dermatology* 126:869-881 (2006).
Lambert, "Molecular Profiling of Cutaneous Squamous Cell Carcinoma," Submitted in fulfilment of the requirements for the degree of Doctor of Philosophy, 328 pages (2010).
Zarovnaya et al., "Distinguishing Pseudoepitheliomatous Hyperplasia From Squamous Cell Carcinoma in Mucosal Biopsy Specimens From the Head and Neck," *Arch Pathol Lab Med* 129:1032-1036 (2005).
Alam et al., "Cutaneous Squamous-Cell Carcinoma," *N Engl J Med*, 344( 13):975-983 (2001).
Smoller, "Squamous cell carcinoma: from precursor lesions to high-risk variants," Department of Pathology, University of Arkansas for Medical Sciences, *Modern Pathology* 19:S88-S92 (2006).
Nindl et al., "Identification of differentially expressed genes in cutaneous squamous cell carcinoma by microarray expression profiling," *Mol Cancer* 5:30 (2006).
Ra et al., "Molecular discrimination of cutaneous squamous cell carcinoma from actinic keratosis and normal skin," *Mod Pathol* 24:963-973 ( 2011).
Alowami et al., "Psoriasin (S100A7) expression is altered during skin tumorigenesis," *BMC Dermatol* 3:1 (2003).
Naidoo et al., "Angiogenesis in cervical cancer is mediated by HeLa metabolites through endothelial cell tissue kallikrein," *Oncol Rep* 22:285-93 (2009).

(Continued)

*Primary Examiner* — Angela M Bertagna
*Assistant Examiner* — Olayinka Oyeyemi
(74) *Attorney, Agent, or Firm* — Suzannah K. Sundby, Esq.; Canady + Lortz LLP

(57) ABSTRACT

Methods for differentiating squamous cell carcinoma from pseudoepitheliomatous hyperplasia in a biological sample using KRT9 and C15orf48, methods of using differentially expressed genes as prognostic markers for squamous cell carcinoma, methods of using molecular pathways as targets for the treatment of squamous cell carcinoma, and diagnostic kits therefor.

14 Claims, 3 Drawing Sheets

(56) References Cited

OTHER PUBLICATIONS

Rückert et al., "Co-expression of KLK6 and KLK10 asprognostic factors for survival in pancreatic ductal adenocarcinoma," *Br J Cancer* 99:1484-92 (2008).

Klucky et al., "Kallikrein 6 induces E-cadherin shedding and promotes cell proliferation, migration, and invasion," *Cancer Res* 67:8198-206 (2007).

Kountourakis et al., "Prognostic value of kallikreinrelated peptidase 6 protein expression levels in advanced ovarian cancer evaluated by automated quantitative analysis (AQUA)," *Cancer Sci* 99:2224-9 (2008).

Nagahara et al., "Clinicopathologic and biological significance of kallikrein 6 overexpression in human gastric cancer," *Clin Cancer Res* 11(19 Pt 1):6800-6 (2005).

Ogawa et al., "Clinical significance of human kallikrein gene 6 messenger RNA expression in colorectal cancer," *Clin Cancer Res* 11:2889-93 (2005).

Anisowicz et al., "A novel protease homolog differentially expressed in breast and ovarian cancer," *Mol Med* 2:624-36 (1996).

Santin et al., "Human kallikrein 6: a new potential serum biomarker for uterine serous papillary cancer," *Clin Cancer Res* 11:3320-5 (2005).

Folgueras et al., "Matrix metalloproteinases in cancer: from new functions to improved inhibition strategies," *Int J Dev Biol* 48:411-24 (2004).

Stokes et al., "Expression profiles and clinical correlations of degradome components in the tumor microenvironment of head and neck squamous cell carcinoma," *Clin Cancer Res* 16: 2022-35 (2010).

Suhr et al., "Gene expression profile of oral squamous cell carcinomas from Sri Lankan betel quid users," *Oncol Rep* 18:1061-75 (2007).

Sova et al., Discovery of novel methylation biomarkers in cervical carcinoma by global demethylation and microarray analysis, *Cancer Epidemic/ Biomarkers Prev* 15:114-23 (2006).

Zhou et al., "A novel gene, NMES1, downregulated in human esophageal squamous cell carcinoma," *Int J Cancer* 101:311-6 (2002).

Razmara et al., CARD-8 protein, a new CARD family member that regulates caspase-1 activation and apoptosis. *J Biol Chem* 277:13952-8 (2002).

Pinto Do O et al., "Hematopoietic progenitor/stem cells immortalized by Lhx2 generate functional hematopoietic cells in vivo," *Blood* 99:3939-46 (2002).

Bloor et al., Expression of keratin K2e in cutaneous and oral lesions: association with keratinocyte activation, proliferation, and keratinization. *Am J Pathol* 162:963-75 (2003).

McCabe et al., "Genome-wide analysis of the homeobox C6 transcriptional network in prostate cancer," *Cancer Res* 68:1988-96 (2008).

Chen et al., "Expression of 11 HOX genes is deregulated in esophageal squamous cell carcinoma," *Clin Cancer Res* 11:1044-9 (2005).

Miller et al., "Aberrant HOXC expression accompanies the malignant phenotype in human prostate," *Cancer Res* 63:5879-88 (2003).

Hasse, The VHL tumor suppressor: master regulator of HI F. *Curr Pharm Des* 15:3895-903 (2009).

Kaelin Jr., Treatment of kidney cancer: insights provided by the VHL tumor-suppressor protein. *Cancer* 115:2262-72 (2009).

Stephen et al., DNA hypermethylation profiles in squamous cell carcinoma of the vulva. *Int J Gynecol Pathol* 28:63-75 (2009).

Asakawa et al., "Tongue cancer patients have a high frequency of allelic loss at the *von Hippel-Lindau* gene and other loci on 3p," *Cancer* 112:527-34 (2008).

Yamamoto et al., "Loss of heterozygosity (LOH) on chromosomes 2q, 3p and 21q in Indian oral squamous cell carcinoma," *Bull Tokyo Dent Coll* 48:109-17 (2007).

Lemaire et al., "Microfibril-associated MAGP-2 stimulates elastic fiber assembly," *J Biol Chem* 282:800-8 (2007).

Spivey et al., A prognostic gene signature in advanced ovarian cancer reveals a microfibril-associated protein (MAGP2) as a promoter of tumor cell survival and angiogenesis. *Cell Adh Migr* 4:169-171 (2010).

Mok et al., "A gene signature predictive for outcome in advanced ovarian cancer identifies a survival factor: microfibril-associated glycoprotein 2," *Cancer Cell* 16:521-32 (2009).

Thorne et al., "The integrins alpha3beta1 and alpha6beta1 physically and functionally associate with CD36 in human melanoma cells," Requirement for the extracellular domain of CD36, *J Biol Chem* 275:35264-75 (2000).

Wong et al., "Identification of molecular markers and signaling pathway in endometrial cancer in Hong Kong Chinese women by genome-wide gene expression profiling," *Oncogene* 26:1971-82 (2007).

Michiels et al., "Genes differentially expressed in medulloblastoma and fetal brain," *Physiol Genomics* 1:83-91 (1999).

Potter et al., "Natriuretic peptides, their receptors, and cyclic guanosine monophosphate-dependent signaling functions," *Endocr Rev* 27:47-72 (2006).

Lu et al., "Implications of mitochondrial DNA mutations and mitochondrial dysfunction in tumorigenesis," *Cell Res* 19: 802-15 (2009).

Carew et al., "Mitochondrial defects in cancer," *Mol Cancer* 1:9 (2002).

Lin et al., "Berberine induces apoptosis in human HSC-3 oral cancer cells via simultaneous activation of the death receptor-mediated and mitochondrial pathway," *Anticancer Res* 27:3371-8 (2007).

Elmets et al., "Targeting ornithine decarboxylase for the prevention of nonmelanoma skin cancer in humans," *Cancer Prev Res (Phila)* 3:8-11 (2010).

Palavan-Unsal et al., "The function of polyamine metabolism in prostate cancer," *Exp Oncol* 28:178-86 (2006).

Wallace et al., "Polyamines and colon cancer," *Eur J Gastroenterol Hepatol* 13:1033-9 (2001).

Bailey et al., "A randomized, double-blind, placebo-controlled phase 3 skin cancer prevention study of {alpha}-difluoromethylornithine in subjects with previous history of skin cancer," *Cancer Prev Res (Phila)* 3:35-47 (2010).

Alberts et al., "Chemoprevention of human actinic keratoses by topical 2-(difluoromethyl)-dl-ornithine," *Cancer Epidemiol Biomarkers Prev* 9:1281-6 (2000).

Nakayama, "Growth and progression of melanoma and non-melanoma skin cancers regulated by ubiquitination," *Pigment Cell Melanoma Res* 23:338-51 (2010).

Galan et al., "Langerhans cells in squamous cell carcinoma vs. pseudoepitheliomatous hyperplasia of the skin," *Journal of Cutaneous Pathology* 34:950-952 (2007).

Lee et al., "p53 expression in pseudoepitheliomatous hyperplasia, keratoacanthoma, and squamous cell carcinoma of skin," *Cancer* 73(9):2317-2323 (1994).

M.H. Grunwald et al., "Pseudocarcinomatous hyperplasia," *Am J Dermapathol* 10:95-103 (1988).

M. Zayour et al., "Pseudoepitheliomatous hyperplasia: a review," *Am J Dermapathol* 33:112-22 (2011).

N. Kluger et al., Pseudoepitheliomatous epidermal hyperplasia in tattoos: a report of three cases, 9 Am J Clin Dermatol 337-40 (2008).

T.P. Dooley et al., "Biomarkers of human cutaneous squamous cell carcinoma from tissues and cell lines identified by DNA microarrays and qRT-PCR," *Biochem Biophys Res Commun* 11:1026-36 (2003).

V.P. Kathpalia et al., "Genome-wide transcriptional profiling in human squamous cell carcinoma of the skin identifies unique tumor-associated signatures," *J Dermtaol* 33:309-18 (2006).

E.D. Emberley et al., "S100 proteins and their influence on pro-survival pathways in cancer," *Biochem Cell Biol.* 82:508-515 (2004).

N. Moubayed et al., "Psoriasin (S100A7) is significantly up-regulated in human epithelial skin tumours," *J Cancer Res Clin Oncol.* 133:253-261 (2007).

I. Salama et al., "A review of the S100 proteins in cancer," *Eur J Surg Oncol.* 34:357-364 (2008).

(56) References Cited

OTHER PUBLICATIONS

K. Oikonomopoulou et al., "Kallikrein-related peptidases: proteolysis and signaling in cancer, the new frontier," *Biol. Chem.* 391:299-310 (2010).
R.S. Henkhaus et al., "Kallikrein 6 is a mediator of K-RAS-dependent migration of colon carcinoma cells," *Biol. Chem.* 389:757-764 (2008).
G. Dorman et al., "Matrix metalloproteinase inhibitors: a critical appraisal of design principles and proposed therapeutic utility," *Drugs* 70:949-964 (2010).
J.M. Freije et al., "Matrix metalloproteinases and tumor progression," *Adv Exp Med Biol.* 532:91-107 (2003).
A. Saleh et al., "Transcriptional profiling of oral squamous cell carcinoma using formalin-fixed paraffin-embedded samples," *Oral Oncol.* 46:379-386 (2010).
G.A. Toruner et al., "Association between gene expression profile and tumor invasion in oral squamous cell carcinoma," *Cancer Genet Cytogenet.* 154:27-35 (2004).
H.K. Wu et at., "Identification of a human LIM-Hox gene, hLH-2, aberrantly expressed in chronic myelogenous leukaemia and located on 9q33-34. 1," *Oncogene* 12:1205-1212 (1996).
J.A. Rothnagel et al., "Mutations in the rod domain of keratin 2e in patients with ichthyosis bullosa of Siemens," *Nat Genet.* 7:485-490 (1994).
A. Reis et al., "Keratin 9 gene mutations in epidermolytic palmoplantar keratoderma (EPPK)," *Nat Genet.* 6:174-179 (1994).
B. Bodey et al., "Immunocytochemical detection of homeobox B3, B4, and C6 gene product expression in lung carcinomas," *Anticancer Res.* 20:2711-2716 (2000).
B. Bodey et al., "Immunocytochemical detection of the homeobox B3, B4, and C6 gene products in breast carcinomas," *Anticancer Res* 20:3281-6 (2000).
C. H. Choi et al., "Hypermethylation and loss of heterozygosity of tumor suppressor genes on chromosome 3p in cervical cancer," *Cancer Lett.* 255:26-33 (2007).
A.R. Albig et al., "Transcriptome analysis of endothelial cell gene expression induced by growth on matrigel matrices: identification and characterization of MAGP-2 and lumican as novel regulators of angiogenesis," *Angiogenesis* 10:197-216 {2007).
M. Chen et al., "Regulation of CD36 expression in human melanoma cells," *Adv Exp Med Bio* 507:337-42 (2002).
J. Aruga et al., "Expression of ZIG family genes in meningiomas and other brain tumors," *BMC Cancer* 10:79 (2010).
L.J. Wang et al., ZIC1 is downregulated through promoter hypermethylation in gastric cancer. Biochem Biophys Res Commun 2009; 379: 959-63.
C.A. Worby et al., "Sorting out the cellular functions of sorting nexins," *Nat Rev Mol Cell Bio* 3:919-3 (2002).
S. Fulda et al., "Targeting mitochondria for cancer therapy," *Nat Rev Drug Discov* 9:447-64 (2010).
M. Zhao et al., "Head and neck cancer cell lines are resistant to mitochondrial-depolarization-induced apoptosis," *ORL J Otorhinolaryngol Relat Spec* 70:257-63 (2008).
S.K. Gilmour, "Polyamines and nonmelanoma skin cancer," *Toxicol Appl Pharmacol* 224:249-56 (2007).
R.A. Casero Jr., "Targeting polyamine metabolism and function in cancer and other hyperproliferative diseases," *Nat Rev Drug Discov* 6:373-90 (2007).
S.R. Ande et al., "The ubiquitin pathway: an emerging drug target in cancer therapy," *Eur J Pharmacol* 625:199-205 (2009).
D. Hoeller et al., "Targeting the ubiquitin system in cancer therapy," *Nature* 458:438-44 (2009).
S.Y. Fuchs, "De-regulation of ubiquitin-dependent proteolysis and the pathogenesis of malignant melanoma," *Cancer Metastasis Rev* 24:329-38 (2005).
D. Hoeller et al., "Ubiquitin and ubiquitin-like proteins in cancer pathogenesis," *Nat Rev Cancer* 26:776-88 (2006).
Office Action (English Translation) dated Apr. 14, 2015 issued in corresponding Chinese Patent Application No. 201280061618.8.

* cited by examiner

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: Left primer sequence for S100A7

<400> SEQUENCE: 1
tgctgacgat gatgaaggag                                             20

<210> SEQ ID NO 2
<211> LENGTH: 20
<212> TYPE: DNA
<213> ORGANISM: Artificial Sequence
<220> FEATURE:
<223> OTHER INFORMATION: Right primer sequence for S100A7

<400> SEQUENCE: 2
atgtctccca gcaaggacag                                             20

<210> SEQ ID NO 3
<211> LENGTH: 20
<212> TYPE: DNA
<213> ORGANISM: Artificial Sequence
<220> FEATURE:
<223> OTHER INFORMATION: Left primer sequence for S100A8

<400> SEQUENCE: 3
gagctggaga aagccttgaa                                             20

<210> SEQ ID NO 4
<211> LENGTH: 20
<212> TYPE: DNA
<213> ORGANISM: Artificial Sequence
<220> FEATURE:
<223> OTHER INFORMATION: Right primer sequence for S100A8

<400> SEQUENCE: 4
agacgtctgc acccttttc                                              20

<210> SEQ ID NO 5
<211> LENGTH: 20
<212> TYPE: DNA
<213> ORGANISM: Artificial Sequence
<220> FEATURE:
<223> OTHER INFORMATION: Left primer sequence for HOXC10

<400> SEQUENCE: 5
gctggtgtgt gtgtcaaacc                                             20

<210> SEQ ID NO 6
<211> LENGTH: 20
<212> TYPE: DNA
<213> ORGANISM: Artificial Sequence
<220> FEATURE:
<223> OTHER INFORMATION: Right primer sequence for HOXC10

<400> SEQUENCE: 6
aacgattctg cctgtgctct                                             20

<210> SEQ ID NO 7
<211> LENGTH: 20
<212> TYPE: DNA
<213> ORGANISM: Artificial Sequence

```
<220> FEATURE:
<223> OTHER INFORMATION: Left primer sequence for C15orf48

<400> SEQUENCE: 7
aagggtgacc aaatgacgag                                                  20

<210> SEQ ID NO 8
<211> LENGTH: 20
<212> TYPE: DNA
<213> ORGANISM: Artificial Sequence
<220> FEATURE:
<223> OTHER INFORMATION: Right primer sequence for C15orf48

<400> SEQUENCE: 8
tgcagttatt gctgcactcc                                                  20

<210> SEQ ID NO 9
<211> LENGTH: 20
<212> TYPE: DNA
<213> ORGANISM: Artificial Sequence
<220> FEATURE:
<223> OTHER INFORMATION: Left primer sequence for KRT9

<400> SEQUENCE: 9
gcctgcttat tggatcctga                                                  20

<210> SEQ ID NO 10
<211> LENGTH: 20
<212> TYPE: DNA
<213> ORGANISM: Artificial Sequence
<220> FEATURE:
<223> OTHER INFORMATION: Right primer sequence for KRT9

<400> SEQUENCE: 10
caggccagag agaggaaaga                                                  20
```

MULTIPLEX PCR-BASED TESTING OF CUTANEOUS SQUAMOUS CELL CARCINOMA AND PSEUDOEPITHELIOMATOUS HYPERPLASIA AND METHODS FOR DISTINGUISHING THE SAME

CROSS-REFERENCE TO RELATED APPLICATIONS

This application is a U.S. National Stage patent application pursuant to 35 U.S.C. §371 of International Patent Application PCT/US2012/059947, filed on Oct. 12, 2012, and published as WO 2013/056042 on Apr. 18, 2013, which claims priority to U.S. Provisional Patent Application Ser. No. 61/547,272 filed on Oct. 14, 2011, the contents of which is incorporated herein by reference for all purposes.

The invention pertains to methods for differentiating cutaneous squamous cell carcinoma from pseudoepitheliomatous hyperplasia in a biological sample, to methods of using differentially expressed genes as prognostic markers for cutaneous squamous cell carcinoma, and to methods of using molecular pathways as targets for the treatment of cutaneous squamous cell carcinoma.

REFERENCE TO A SEQUENCE LISTING SUBMITTED VIA EFS-WEB

The content of the ASCII text file of the sequence listing named "20161004_034044_160US1_seq_ST25" which is 2.44 kb in size was created on Oct. 4, 2016, and electronically submitted via EFS-Web on Oct. 4, 2016, is incorporated herein by reference in its entirety.

BACKGROUND OF THE INVENTION

Cutaneous squamous cell carcinoma is the second most common cutaneous malignancy with over 250,000 cases diagnosed per year. See M. Alam and D. Ratner, *Cutaneous squamous cell carcinoma*, 344 N ENG J MED 975-83 (2001). Although it is typically a straightforward diagnosis, there are many clinical and histologic simulants of cutaneous squamous cell carcinoma. Some of the lesions that can be the most difficult to differentiate, such as actinic keratosis and squamous cell carcinoma in-situ, display varying different degrees of keratinocyte dysplasia and are typically considered neoplastic precursors to squamous cell carcinoma. See B. R. Smoller, *Squamous cell carcinoma: from precursor lesions to high-risk variants*, 19 Suppl 2 MOD PATHOL (S88-92) (2006).

One of the most difficult lesions to differentiate from squamous cell carcinoma is pseudoepitheliomatous hyperplasia. Pseudoepitheliomatous hyperplasia is a hyperplastic squamoid proliferation typically associated with an inflammatory or neoplastic process. See M. H. Grunwald et al., *Pseudocarcinomatous hyperplasia*, 10 AM J DERMATOPATHOL 95-103 (1988); M. Zayour and R. Lazova, *Pseudoepitheliomatous hyperplasia: a review*, 33 AM J DERMATOPATHOL 112-22 (2011). Pseudoepitheliomatous hyperplasia can be seen in association with inflammatory infiltrates due to chronic ulceration with re-epithelialization, infection, and tattoo pigment. See M. H. Grunwald et al., *Pseudocarcinomatous hyperplasia*, 10 AM J DERMATOPATHOL 95-103 (1988); M. Zayour and R. Lazova, *Pseudoepitheliomatous hyperplasia: a review*, 33 AM J DERMATOPATHOL 112-22 (2011); N. Kluger et al., *Pseudoepitheliomatous epidermal hyperplasia in tattoos: a report of three cases*, 9 AM J CLIN DERMATOL 337-40 (2008). It has also been described in association with granular cell tumor, dermatofibroma, Spitz tumor, and melanoma. See M. H. Grunwald et al., *Pseudocarcinomatous hyperplasia*, 10 AM J DERMATOPATHOL 95-103 (1988); M. Zayour and R. Lazova, *Pseudoepitheliomatous hyperplasia: a review*, 33 AM J DERMATOPATHOL 112-22 (2011).

Histologically, pseudoepitheliomatous hyperplasia is characterized by irregular extension into the dermis by nests and strands of squamoid cells with jagged edges that may proliferate in a poorly circumscribed manner and display nuclear atypia and mitoses. Although morphologic criteria for differentiating between squamous cell carcinoma and pseudoepitheliomatous hyperplasia have been delineated, distinguishing between them may be difficult or nearly impossible in some circumstances especially in superficial, limited, or poorly oriented biopsies. See M. H. Grunwald et al., *Pseudocarcinomatous hyperplasia*, 10 AM J DERMATOPATHOL 95-103 (1988); M. Zayour and R. Lazova, *Pseudoepitheliomatous hyperplasia: a review*, 33 AM J DERMATOPATHOL 112-22 (2011); N. Kluger et al., *Pseudoepitheliomatous epidermal hyperplasia in tattoos: a report of three cases*, 9 AM J CLIN DERMATOL 337-40 (2008).

Because squamous cell carcinoma is one of the most commonly diagnosed cutaneous malignancies, because its accurate diagnosis is often challenging, and because clinical management of patients is largely dependent on pathologic diagnostic accuracy, there exists a need for a reliable method for accurately distinguishing between squamous cell carcinoma and pseudoepitheliomatous hyperplasia, thereby leading to accurate diagnoses and appropriate treatment.

SUMMARY OF THE INVENTION

The distinctive gene expression profile of squamous cell carcinoma and pseudoepitheliomatous hyperplasia now offers the ability to utilize DNA microarrays to distinguish between the two by an objective molecular measure.

The instant invention provides a method for differentiating cutaneous squamous cell carcinoma from pseudoepitheliomatous hyperplasia in a biological sample by isolating total RNA from said sample, performing multiplex PCR using KRT9 and C15orf48 probes/primers and said isolated RNA, obtaining a CT value for KRT9, and obtaining a CT value for C15orf48. If the CT value of C15orf48 is lower than the CT value of KRT9, then the sample is cutaneous squamous cell carcinoma. If the CT value of C15orf48 is higher than the CT value of KRT9, then the sample is pseudoepitheliomatous hyperplasia.

The instant invention also provides methods of using differentially expressed genes as prognostic markers for cutaneous squamous cell carcinoma.

The instant invention also provides methods of using molecular pathways, such as oxidative phosphorylation, polyamine regulation in colon cancer, mitochondrial dysfunction, and protein ubiquitination, as targets for the treatment of cutaneous squamous cell carcinoma.

DETAILED DESCRIPTION OF THE INVENTION

Figure 1:
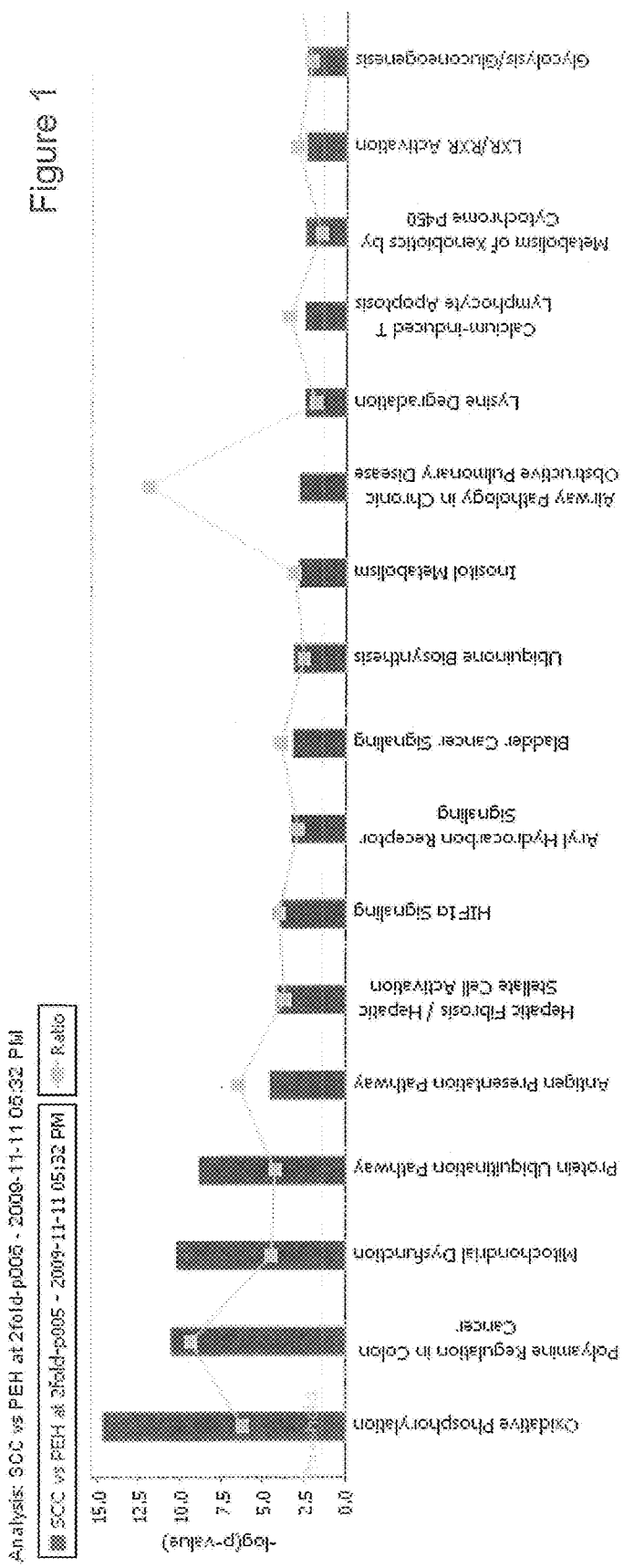
FIG. 1 depicts the most significantly enriched molecular pathways (x axis) comparing squamous cell carcinoma versus pseudoepitheliomatous hyperplasia (FC>2.0, P<0.05) utilizing the [−log (P-value)] on the y axis. The horizontal line represents the threshold for significance (P<0.05).

Prior to the instant invention there were but a few DNA microarray studies that examined differential gene expression between cutaneous squamous lesions. See T. P. Dooley et al., *Biomarkers of human cutaneous squamous cell carcinoma from tissues and cell lines identified by DNA microarrays and qRT-PCR*, 11 BIOCHEM BIOPHYS RES COMMUN 1026-36 (2003); A. S. Haider et al., *Genomic analysis defines a cancer-specific gene expression signature for human squamous cell carcinoma and distinguishes malignant hyperproliferation from benign hyperplasia*, 126 J INVEST DERMATOL 869-81 (2006); V. P. Kathpalia et al., *Genome-wide transcriptional profiling in human squamous cell carcinoma of the skin identifies unique tumor-associated signatures*, 33 J DERMATOL 309-18 (2006); I. Nindl et al., *Identification of differentially expressed genes in cutaneous squamous cell carcinoma by microarray expression profiling*, 5 MOL CANCER 30 (2006); S. H. Ra et al., *Molecular discrimination of cutaneous squamous cell carcinoma from actinic keratosis and normal skin*, MOD PATHOL (2011) (Advance online publication, Apr. 1, 2011).

The inventors examined the differentially-expressed genes and molecular pathways in comparing squamous cell carcinoma to actinic keratosis and normal skin. See S. H. Ra et al., *Molecular discrimination of cutaneous squamous cell carcinoma from actinic keratosis and normal skin*, MOD PATHOL (2011) (Advance online publication, Apr. 1, 2011). The inventors determined that each of these entities demonstrated a unique molecular signature. The inventors, as detailed below, profiled and examined the gene expression of over 47,000 genes using one of the most comprehensive GeneChip microarrays available (human U133 plus 2.0 array) to study differential gene expression between squamous cell carcinoma and pseudoepitheliomatous hyperplasia in formalin-fixed paraffin-embedded tissue.

Based on these studies, the inventors determined that the distinctive gene expression profile of squamous cell carcinoma and pseudoepitheliomatous hyperplasia now offers the ability to utilize DNA microarrays to distinguish between the two by an objective molecular measure.

The instant invention provides a method for differentiating cutaneous squamous cell carcinoma from pseudoepitheliomatous hyperplasia in a biological sample, such as one obtained from a human, by isolating total RNA from said sample, performing multiplex PCR using KRT9 and C15orf48 probes/primers and said isolated RNA, obtaining a CT value for KRT9, and obtaining a CT value for C15orf48. If the CT value of C15orf48 is lower than the CT value of KRT9, then the sample is cutaneous squamous cell carcinoma. If the CT value of C15orf48 is higher than the CT value of KRT9, then the sample is pseudoepitheliomatous hyperplasia.

The instant invention also provides diagnostic kits for assaying a biological sample, such as those obtained from a human. The kits include an agent for detecting KRT9, an agent for detecting C15orf48, one or more reagents useful for facilitating said detection, and instructions for use of said kit.

The instant invention also provides methods of using differentially expressed genes as prognostic markers for cutaneous squamous cell carcinoma.

The instant invention also provides methods of using molecular pathways, such as oxidative phosphorylation, polyamine regulation in colon cancer, mitochondrial dysfunction, and protein ubiquitination, as targets for the treatment of cutaneous squamous cell carcinoma.

Other characteristics and advantages of the invention appear in the examples and figures.

The invention is described in more detail in the following illustrative examples. Although the examples may represent only selected embodiments of the invention, the following examples are illustrative only and in no way limiting.

EXAMPLES

Example 1: Analysis of Squamous Cell Carcinomas and Pseudoepitheliomatous Hyperplasia Ten cases of squamous cell carcinomas and ten cases of pseudoepitheliomatous hyperplasia, inflammatory type, were identified from the Tamtron database. The slides and formalin-fixed paraffin-embedded tissue (<6 months old) were retrieved. The slides were reviewed and their diagnoses confirmed. The areas of interest were removed from the paraffin blocks with a sterile surgical scalpel.

RNA Isolation and Quality Control

Total RNA was isolated using the Ambion® Recover-All™ (Applied Biosystems/Ambion,® Austin, Tex., USA) kit according to the manufacturer's instructions. Briefly, formalin-fixed and paraffin-embedded samples were deparaffinized using a series of xylene and ethanol washes, and then subjected to a proteinase K digestion at 50° C. for 16 hours to release RNA from covalently linked proteins. Finally, total RNA was purified by capture on a glass-fiber filter. After washing, the total RNA was eluted. RNA Integrity was evaluated using an Agilent 2100 Bioanalyzer (Agilent Technologies, Palo Alto, Calif., USA) and purity/concentration was determined using a NanoDrop™ 8000 (NanoDrop Products, Wilmington, Del., USA). The RNA samples with RNA Integrity Number (RIN)≥5 and 260/280 ratio≥1.7 were selected for the microarray.

Target Preparation and Microarray Hybridization

Microarray targets were prepared using NuGEN WT-Ovation® formalin-fixed and paraffin-embedded RNA Amplification System V2. This system offers efficient cDNA amplification powered by Ribo-SPIA® technology. It is therefore ideal for global gene expression analysis with the small amount of degraded RNA derived from formalin-fixed and paraffin-embedded samples. Fifty nanograms of total RNA were used for the first strand synthesis. After the second strand cDNA synthesis, the double stranded cDNA was purified using Agencourt® RNAClean® beads provided with the WT-Ovation kit, followed by SPIA cDNA Amplification. Five micrograms of amplified cDNA was fragmented and labeled using NuGEN's FL-Ovation® cDNA Biotin Module V2 according to the instructions (NuGEN® Technologies, San Carlos, Calif., USA), and then hybridized to the Affymetrix GeneChip® U133plus 2.0 Array (Affymetrix Inc., Santa Clara, Calif., USA) according to manufacturers' instructions. The arrays were washed and stained with streptavidin phycoerythrin in Affymetrix Fluidics Station 450 using the Affymetrix GeneChip® protocol and scanned using an Affymetrix GeneChip® Scanner 3000.

Data Analysis

The acquisition and initial quantification of array images were conducted using the AGCC software (Affymetrix, Santa Clara, Calif., USA). Subsequent data analyses were performed using Partek® Genomics Suite Version 6.4 (Partek® Inc., St. Louis, Mo., USA). First, a one-way ANOVA was performed to identify genes between groups at p<0.05, and then calculated relative difference in fold change between groups. The genes at ≥2 fold and p<0.05 were considered as differentially expressed between groups. Cluster analyses were conducted with Partek® default settings. The canonical pathway analyses were performed using Ingenuity Pathway Analysis Version 7.6 (Ingenuity Systems®, Redwood City, Calif., USA). Briefly, a differentially expressed gene list containing gene identifiers and corresponding fold changes was first uploaded as an Excel spreadsheet into the software. Each gene identifier was mapped to its corresponding gene object in the Ingenuity Pathways Knowledge Base. These genes were then used as the starting point for pathway analysis. Canonical pathways analysis identified the pathways from the Ingenuity Pathways Analysis library of canonical pathways that were most significant to the data set. The significance of the association between the data set and the canonical pathway was measured in 2 ways: 1) A ratio of the number of genes from the data set that map to the pathway divided by the total number of genes that map to the canonical pathway was displayed; and 2) Fischer's exact test was used to calculate a p-value determining the probability that the association between the genes in the dataset and the canonical pathway is explained by chance alone.

Quantitative Real Time PCR Analyses

QRT-PCR confirmation was performed using SYBR Green real-time RT-PCR kit (Applied Biosystems) according to the manufacturer's instructions. The same RNAs for microarray hybridization were used for QRT-PCR confirmation. *Applied Biosystems* 7500 *Real-Time PCR* System was used for the analyses with the following primers:

```
S100A7:    Left  tgctgacgatgatgaaggag; (SEQ ID NO: 1)
           Right atgtctcccagcaaggacag  (SEQ ID NO: 2)

S100A8:    Left  gagctggagaaagccttgaa; (SEQ ID NO: 3)
           Right agacgtctgcacccttttc   (SEQ ID NO: 4)

HOXC10:    Left  gctggtgtgtgtgtcaaacc; (SEQ ID NO: 5)
           Right aacgattctgcctgtgctct  (SEQ ID NO: 6)

C15orf48:  Left  aagggtgaccaaatgacag;  (SEQ ID NO: 7)
           Right tgcagttattgctgcactcc  (SEQ ID NO: 8)

KRT9:      Left  gcctgcttattggatcctga; (SEQ ID NO: 9)
           Right caggccagagagaggaaaga  (SEQ ID NO: 10)
```

GAPDH was used as an internal control for normalization.

Data 703 differentially expressed genes were identified between SCC and PEH, of which 657 were upregulated and 46 were downregulated. The Pathway analysis revealed that the most significantly enriched molecular pathways among these 703 genes were oxidative phosphorylation, polyamine regulation in colon cancer, mitochondrial dysfunction, and protein ubiquitination. See FIG. 1.

The most significantly upregulated genes included C15orf48, KLK6, CARD18, MMP1, LHX2, and the calcium binding proteins: S100A7, S100A7A, S100A8, S100A9, and S100P. The most significantly downregulated genes included KRT9, KRT2, SNX21, HOXC6, VHL, CD36, MFAP5, HOXC10, ZIC1, and NPR3. See Table 1.

TABLE I

Differentially expressed genes distinguishing squamous cell carcinoma and pseudoepitheliomatous hyperplasia

| RefSeq | Symbol/Gene | Fold Change |
|---|---|---|
| UPREGULATED GENES | | |
| NM_002964 | S100A8: S100 calcium binding protein A8 | 13.07 |
| NM_032413 /// NM_197955 | C15orf48: chromosome 15 open reading frame 48 | 10.99 |
| NM_002963 | S100A7: S100 calcium binding protein A7 | 9.73 |
| NM_002965 | S100A9: S100 calcium binding protein A9 | 9.44 |
| NM_176823 | S100A7A: S100 calcium binding protein A7A | 7.37 |
| NM_001012964 /// NM_001012965 /// NM_002774 | KLK6: kallikrein-related peptidase 6 | 5.87 |
| NM_021571 | CARD18: caspase recruitment domain family, member 18 | 5.70 |
| NM_001145938 /// NM_002421 | MMP1: matrix metallopeptidase 1 (interstitial collagenase) | 5.41 |
| NM_004789 | LHX2: LIM homeobox 2 | 5.40 |
| NM_005980 | S100P: S100 calcium binding protein P | 5.30 |
| DOWNREGULATED GENES | | |
| NM_000226 | KRT9: keratin 9 | −15.30 |
| NM_000423 | KRT2: keratin 2 | −6.00 |
| NM_001042632 /// NM_001042633 /// NM_033421 /// NM_152897 | SNX21: sorting nexin family member 21 | −3.20 |
| NM_004503 /// NM_153693 | HOXC6: homeobox C6 | −3.19 |
| NM_000551 /// NM_198156 | VHL: von Hippel-Lindau tumor suppressor | −2.81 |
| NM_000072 /// NM_001001547 /// NM_001001548 /// NM_001127443 /// NM_001127444 | CD36: CD36 molecule (thrombospondin receptor) | −2.77 |
| NM_003480 | MFAP5: microfibrillar associated protein 5 | −2.56 |
| NM_017409 | HOXC10: homeobox C10 | −2.55 |
| NM_003412 | ZIC1: Zic family member 1 (odd-paired homolog, *Drosophila*) | −2.48 |
| NM_000908 | NPR3: natriuretic peptide receptor C/guanylate cyclase C (atrionatriuretic peptide rec | −2.47 |

Figure 2:
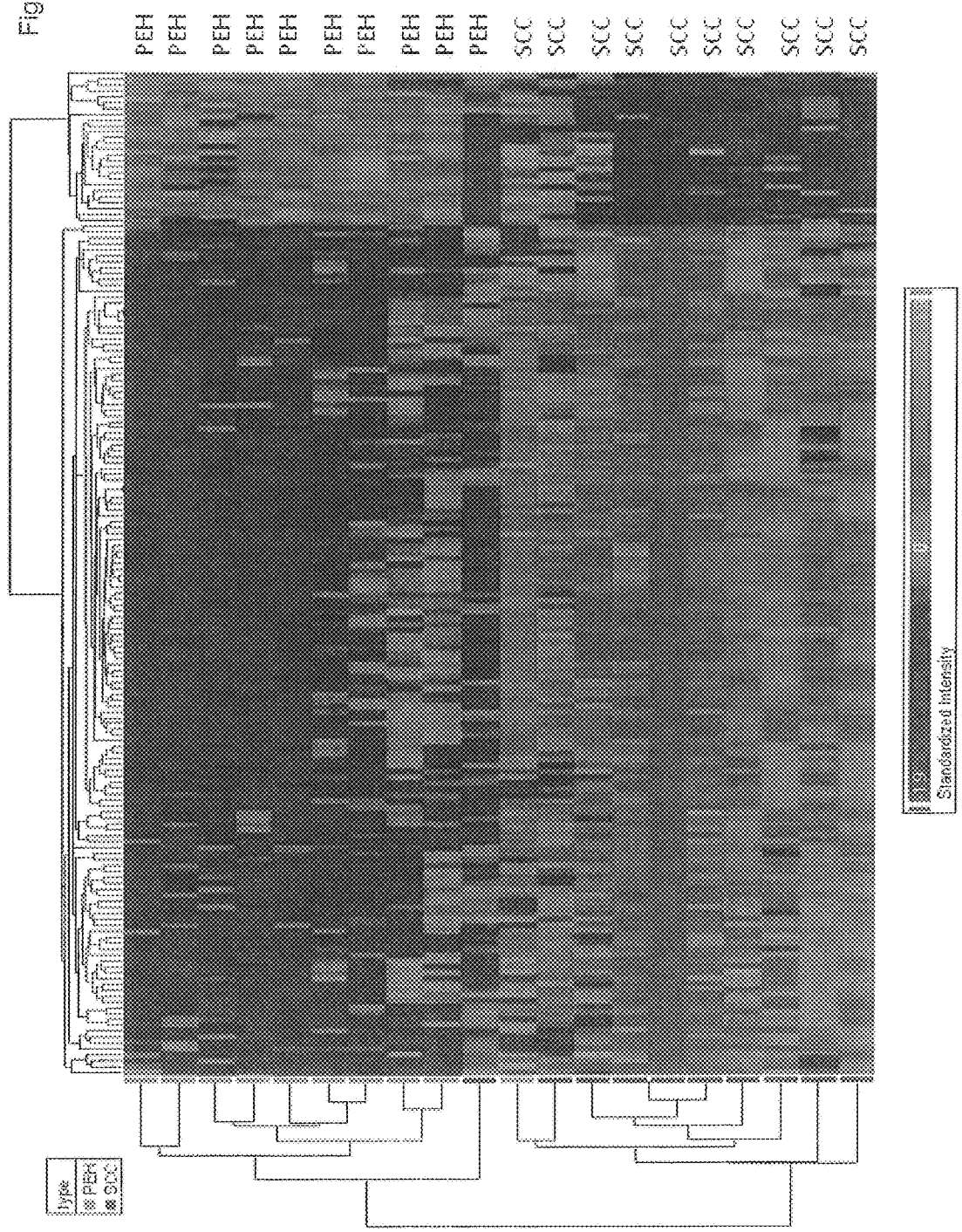
FIG. 2 depicts an hierarchical cluster analysis using the most significant differentially expressed genes (y axis) that revealed squamous cell carcinoma (SCC) and pseudoepitheliomatous hyperplasia (PEH; x axis) demonstrated distinct genetic signatures.

Hierarchical cluster analysis utilizing the most significant differentially expressed genes revealed that squamous cell carcinoma and pseudoepitheliomatous hyperplasia have a distinct genetic signature. See FIG. 2.

Figure 3:
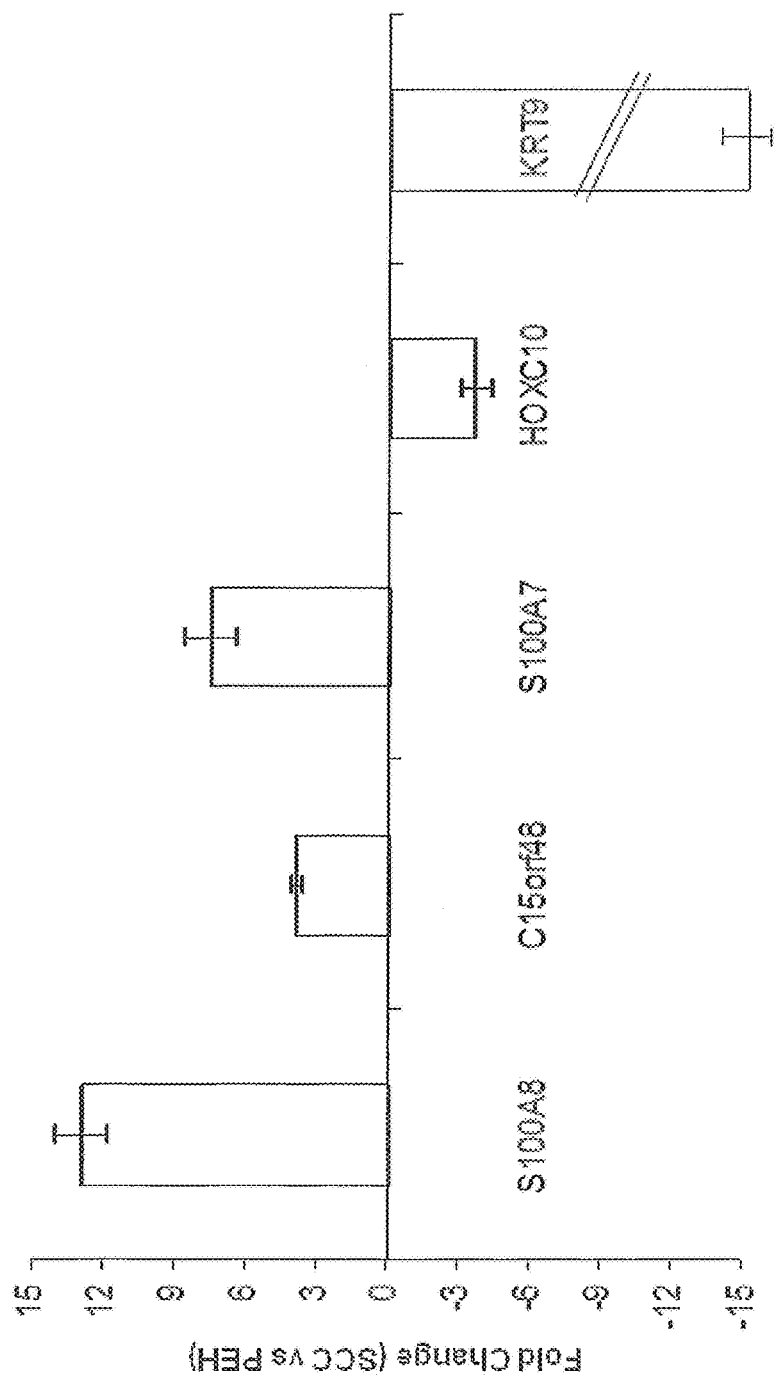
FIG. 3 depicts QRT-PCR analyses confirming differential expression of five representative genes between squamous cell carcinoma and pseudoepitheliomatous hyperplasia. The y axis represents fold change (squamous cell carcinoma versus pseudoepitheliomatous hyperplasia). The bar on the column stands for the standard deviation.

To confirm the reliability of the results from microarray analysis, selected upregulated genes including S100A7, S100A8, and C15orf48 and downregulated genes including HOXC10 and KRT9 were verified by QRT-PCR analyses. See FIG. 3.

Discussion

Squamous cell carcinoma and pseudoepitheliomatous hyperplasia can look virtually identical clinically and histologically. However, the pathogenesis of these lesions are dissimilar. Squamous cell carcinoma is a neoplastic process and pseudoepitheliomatous hyperplasia is believed to be a reactive process. See M. H. Grunwald et al., *Pseudocarcinomatous hyperplasia*, 10 AM J DERMATOPATHOL 95-103 (1988). Prior to the instant invention there were no reliable ancillary discriminatory immunohistochemical or molecular tests available to differentiate between these lesions. Using DNA microarrays, it was determined that squamous cell carcinoma and pseudoepitheliomatous hyperplasia are distinct lesions with unique molecular signatures. The instant invention provides the ability to distinguish squamous cell carcinoma and pseudoepitheliomatous hyperplasia due to the identification of differentially expressed genes and enriched molecular pathways.

The genes for calcium binding proteins S100A7, S100A7A, S100A8, S100A9, and S100P were significantly upregulated in squamous cell carcinoma in comparison to pseudoepitheliomatous hyperplasia (FC=9.73, 7.37, 13.07, 9.44, 5.30). The S100 family of proteins is defined by their structural calcium-binding motifs. S100 proteins are localized in the cytoplasm and/or nucleus of a wide range of cells, and involved in the regulation of a number of cellular processes such as cell cycle progression, differentiation, the immune response, cytoskeleton dynamics, enzyme activity, $Ca^{2+}$ homeostasis, and growth. See, e.g., E. D. Emberley et al., *S100 proteins and their influence on pro-survival pathways in cancer*, 82 BIOCHEM CELL BIOL. 508-515 (2004). A potential role for tumorigenesis arises from alteration in these pathways. A previous microarray study comparing squamous cell carcinoma to normal skin demonstrated upregulation of calcium binding proteins S100A8 and S100A9. See S. H. Ra et al., *Molecular discrimination of cutaneous squamous cell carcinoma from actinic keratosis and normal skin*, MOD PATHOL (2011) (Advance online publication, Apr. 1, 2011). Other RT-PCR and immunohistochemical studies revealing significant upregulation/overexpression of S100A7 in cutaneous squamous cell carcinomas supports these microarray findings. See S. Alowami et al., *Psoriasin (S100A7) expression is altered during skin tumorigenesis*, 3 BMC DERMATOL. 1(2003); N. Moubayed et al., *Psoriasin (S100A7) is significantly up-regulated in human epithelial skin tumours*, 133 J CANCER RES CLIN ONCOL. 253-261 (2007). Calcium binding proteins play a role not only in the pathogenesis of cutaneous squamous cell carcinoma, but in other malignancies as well. The altered expression/upregulation of the calcium binding protein in the S100 family has been observed in many cancers including breast, lung, bladder, kidney, thyroid, gastric, prostate, and oral cancers. See I. Salama et al., *A review of the S100 proteins in cancer*, 34 Eur J Surg Oncol. 357-364 (2008).

KLK6 was found to be overexpressed with a FC of 5.87. KLK6 is part of the family serine proteases that have hormonal properties by signaling through proteinase-activated receptors that participate in cell proliferation, cytokine release, vascular relaxation, platelet aggregation, and inflammation. See K. Oikonomopoulou et al., *Kallikrein-related peptidases: proteolysis and signaling in cancer, the new frontier*, 391 BIOL CHEM. 299-310 (2010). Tumorigenesis is postulated to be mediated by promotion of cell proliferation, migration, and angiogenesis. See S. Naidoo and D. M. Raidoo, *Angiogenesis in cervical cancer is mediated by HeLa metabolites through endothelial cell tissue kallikrein*, 22 ONCOL REP. 285-293 (2009); F. Rückert et al., *Co-expression of KLK6 and KLK10 as prognostic factors for survival in pancreatic ductal adenocarcinoma*, 99 BR J CANCER. 1484-1492 (2008). Increased expression of KLK6 in cutaneous squamous cell carcinoma was demonstrated by one immunohistochemical study. See B. Klucky et al., *Kallikrein 6 induces E-cadherin shedding and promotes cell proliferation, migration, and invasion*, 67 CANCER RES. 8198-8206 (2007). The differential expression of KLK6 has been implicated in wide variety of carcinomas of ovarian, gastric, pancreatic, breast, uterine, and colon origin. See A. Anisowicz et al., *A novel protease homolog differentially expressed in breast and ovarian cancer*, 2 MOL. MED. 624-636 (1996); R. S. Henkhaus et al., *Kallikrein 6 is a mediator of K-RAS-dependent migration of colon carcinoma cells*, 389 BIOL CHEM. 757-764 (2008); P. Kountourakis et al., *Prognostic value of kallikrein-related peptidase 6 protein expression levels in advanced ovarian cancer evaluated by automated quantitative analysis (AQUA)*, 99 CANCER SCI. 2224-2229 (2008); H. Nagahara et al., *Clinicopathologic and biological significance of kallikrein 6 overexpression in human gastric cancer*, 11(19 Pt 1) CLIN CANCER RES. 6800-6806 (2005); S. Naidoo and D. M. Raidoo, *Angiogenesis in cervical cancer is mediated by HeLa metabolites through endothelial cell tissue kallikrein*, 22 ONCOL REP. 285-293 (2009); K. Ogawa et al., *Clinical significance of human kallikrein gene 6 messenger RNA expression in colorectal cancer*, 11 CLIN CANCER RES. 2889-2893 (2005); F. Rückert et al., *Co-expression of KLK6 and KLK10 as prognostic factors for survival in pancreatic ductal adenocarcinoma*, 99 BR J CANCER. 1484-1492 (2008); A. D. Santin et al., *Human kallikrein 6: a new potential serum biomarker for uterine serous papillary cancer*, 11 CLIN CANCER RES. 3320-3325 (2005). KLK6 upregulation has been associated with a poor prognosis in gastric, ovarian, and pancreatic carcinomas. See P. Kountourakis et al., *Prognostic value of kallikrein-related peptidase 6 protein expression levels in advanced ovarian cancer evaluated by automated quantitative analysis (AQUA)*, 99 CANCER SCI. 2224-2229 (2008); H. Nagahara et al., *Clinicopathologic and biological significance of kallikrein 6 overexpression in human gastric cancer*, 11(19 Pt 1) CLIN CANCER RES. 6800-6806 (2005); F. Rückert et al., *Co-expression of KLK6 and KLK10 as prognostic factors for survival in pancreatic ductal adenocarcinoma*, 99 BR J CANCER. 1484-1492 (2008).

MMP1 was found to be overexpressed with an FC of 5.41. MMP1 is one of the proteins of the matrix metalloproteinase family that are involved in the breakdown of extracellular matrix in normal physiological processes, such as embryonic development, reproduction, and tissue remodeling. See G. Dormán et al., *Matrix metalloproteinase inhibitors: a critical appraisal of design principles and proposed therapeutic utility*, 70 DRUGS 949-964 (2010); A. R. Folgueras et al., *Matrix metalloproteinases in cancer: from new functions to improved inhibition strategies*, 48 INT J DEV BIOL. 411-424 (2004). Matrix metalloproteinases play an important role in tumorigenesis through the proteolytic destruction of extracellular matrix and basement membranes and facilitation of tumor invasion and metastasis. See A. R. Folgueras et al., *Matrix metalloproteinases in cancer: from new functions to improved inhibition strategies*, 48 INT J DEV BIOL. 411-424 (2004); J. M. Freije et al., *Matrix metalloproteinases and tumor progression*, 532 ADV EXP MED BIOL. 91-107 (2003). MMP1 was the most overexpressed gene in the microarray study (FC=48.51) comparing squamous cell carcinoma to normal skin. See S. H. Ra et al., *Molecular discrimination of cutaneous squamous cell carcinoma from actinic keratosis and normal skin*, MOD PATHOL (2011) (Advance online publication, Apr. 1, 2011). MMP1 is one of the rare genes consistently overexpressed in the different microarray studies examining cutaneous SCCs in comparison to normal skin. See A. S. Haider et al., *Genomic analysis defines a cancer-specific gene expression signature for human squamous cell carcinoma and distinguishes malignant* hyperproliferation from benign hyperplasia, 126 J INVEST DERMATOL. 869-881 (2006); I. Nindl et al., *Identification of differentially expressed genes in cutaneous squamous cell carcinoma by microarray expression profiling*, 5 MOD CANCER. 30 (2006); S. H. Ra et al., *Molecular discrimination of cutaneous squamous cell carcinoma from actinic keratosis and normal skin*, MOD PATHOL (2011) (Advance online publication, Apr. 1, 2011). Upregulation of MMP1 appears to be conserved in squamous cell carcinomas from different anatomic locations including the head, neck, and oral cavity and may play a crucial role in the pathogenesis of squamous cell carcinoma. See A. Saleh et al., *Transcriptional profiling of oral squamous cell carcinoma using formalin-fixed paraffin-embedded samples*, 46 ORAL ONCOL. 379-386 (2010); A. Stokes et al., *Expression profiles and clinical correlations of degradome components in the tumor microenvironment of head and neck squamous cell carcinoma*, 16 CLIN CANCER RES. 2022-2035 (2010); M. L. Suhr et al., *Gene expression profile of oral squamous cell carcinomas from Sri Lankan betel quid users*, 18 ONCOL REP. 1061-1075 (2007); G. A. Toruner et al., *Association between gene expression profile and tumor invasion in oral squamous cell carcinoma*, 154 CANCER GENET CYTOGENET. 27-35 (2004).

C15orf48, CARD18, and LSX2 were also found to be significantly upregulated (FC=10.99, 5.70, and 5.40). The function of C15orf48 (NMES1) plays a role in the pathogenesis of squamous cell carcinoma. Downregulation of C15orf48 (NMES1) has been demonstrated in esophageal squamous cell carcinomas and its aberrant methylation reported in cervical squamous cell carcinoma cell lines. See P. Soya et al., *Discovery of novel methylation biomarkers in cervical carcinoma by global demethylation and microarray analysis*, 15 CANCER EPIDEMIOL BIOMARKERS PREV. 114-123 (2006); J. Zhou et al., *A novel gene, NMES1, downregulated in human esophageal squamous cell carcinoma*, 101 INT J CANCER. 311-316 (2002). CARD18 belongs to a family of caspase-associated recruitment domains (CARD) that act as protein-protein interaction modules found extensively in proteins that play important roles in apoptosis, NFkappaB activation, and cytokine regulation. See M. Razmara et al., *CARD-8 protein, a new CARD family member that regulates caspase-1 activation and apoptosis*, 277 J BIOL CHEM. 13952-13958 (2002). Deregulation of these pathways may lead to tumorigenesis. LHX2 is transcriptional regulatory protein involved in the control of cell differentiation in developing lymphoid and neural cell types. LHX2 has been found to immortalize multipotent hematopoietic progenitor/stem cells. See O. P. Pinto do et al., *Hematopoietic progenitor/stem cells immortalized by Lhx2 generate functional hematopoietic cells in vivo*, 99 BLOOD 3939-3946 (2002). Its upregulation has been identified in chronic myelogenous leukemia. See H. K. Wu et al., *Identification of a human LIM-Hox gene, hLH-2, aberrantly expressed in chronic myelogenous leukaemia and located on 9q33-34.1.*, 12 ONCOGENE. 1205-1212 (1996).

The most significantly downregulated genes between squamous cell carcinoma and pseudoepitheliomatous hyperplasia were KRT9 and KRT2 (FC=−15.30 and −6.00). Keratins form an intracellular keratin filament network within keratinocytes. Loss of regulation of this network may be needed for the evolution of squamous cell carcinoma from normal skin. KRT2 is believed to contribute to keratinocyte terminal cornification and is associated with keratinocyte activation, proliferation and keratinization. Like the foregoing, an immunohistochemical study on cutaneous squamous cell carcinomas revealed loss of expression of KRT2. See B. K. Bloor et al., *Expression of keratin K2e in cutaneous and oral lesions: association with keratinocyte activation, proliferation, and keratinization*, 162 AM J PATHOL. 963-975 (2003). Mutations in the KRT2 genes have also been associated with ichthyosis bullosa of Siemens. See J. A. Rothnagel et al., *Mutations in the rod domain of keratin 2e in patients with ichthyosis bullosa of Siemens*, 7 NAT GENET. 485-490 (1994). KRT9 encodes an intermediate filament chain expressed only in the terminally differentiated epidermis of palms and soles. Mutations in this gene cause epidermolytic palmoplantar keratoderma. See A. Reis et al., *Keratin 9 gene mutations in epidermolytic palmoplantar keratoderma (EPPK)*, 6 NAT GENET. 174-179 (1994). Its role in tumorigenesis is unknown and had not previously been associated with squamous cell carcinoma.

The homeobox genes HOX6 and HOX10 were downregulated (FC=−3.19 and −2.55). These genes encode homeobox transcription factors that play vital roles in the genetic control of multiple genes involved in development and cell differentiation. Re-expression of HOX gene products has been reported in a wide variety of neoplastically transformed cells and they may represent another class of oncofetal antigens involved in normal development and cellular carcinogenesis, as well as tumor progression. See B. Bodey et al., *Immunocytochemical detection of homeobox B3, B4, and C6 gene product expression in lung carcinomas*, 20 ANTICANCER RES. 2711-2716 (2000). Although HOX6 has been found to be upregulated in carcinomas of prostate, breast, lung, and esophageal origin, it was downregulated in the foregoing study. See B. Bodey et al., *Immunocytochemical detection of homeobox B3, B4, and C6 gene product expression in lung carcinomas*, 20 ANTICANCER RES. 2711-2716 (2000); B. Bodey et al., *Immunocytochemical detection of the homeobox B3, B4, and C6 gene products in breast carcinomas*, 20 ANTICANCER RES. 3281-3286 (2000); K. N. Chen et al., *Expression of 11 HOX genes is deregulated in esophageal squamous cell carcinoma*, 11 CLIN CANCER RES. 1044-1049 (2005); C. D. McCabe et al., *Genome-wide analysis of the homeobox C6 transcriptional network in prostate cancer*, 68 CANCER RES. 1988-1996 (2008); G. J. Miller et al., *Aberrant HOXC expression accompanies the malignant phenotype in human prostate*, 63 CANCER RES. 5879-5888 (2003). HOX10 has not been described in association with malignancy.

The downregulated genes VHL and MFAP5 (FC=−2.81 and −2.56) have been described in association with squamous cell carcinoma. VHL is a tumor suppressor gene that plays an important role in the regulation of cell growth and differentiation of human kidney cells. Inactivation of VHL is linked to the hereditary Von Hippel Lindau disease characterized by central nervous system hemangioblastomas, clear cell renal cell carcinomas and pheochromocytomas. See V. H. Haase, *The VHL tumor suppressor: master regulator of HIF*, 15 CURR PHARM DES. 3895-3903 (2009); W. G. Kaelin, *Treatment of kidney cancer: insights provided by the VHL tumor-suppressor protein*, 115 CANCER 2262-2272 (2009). VHL is also frequently mutated in sporadic renal cell carcinomas. Id. Several abnormalities of the VHL gene including abnormal DNA methylation and loss of heterozygosity of chromosome 3p has been identified in SCCs from the cervix, vulva, tongue, and oral cavity. See T. Asakawa et al., *Tongue cancer patients have a high frequency of allelic loss at the von Hippel-Lindau gene and other loci on 3p*, 112 CANCER 527-534 (2008); C. H. Choi et al., *Hypermethylation and loss of heterozygosity of tumor suppressor genes on chromosome 3p in cervical cancer*, 255 CANCER LETT. 26-33 (2007); J. K. Stephen et al., *DNA hypermethylation profiles in squamous cell carcinoma of the vulva*, 28 INT J GYNECOL PATHOL. 63-75 (2009); N. Yamamoto et al., *Loss of heterozygosity (LOH) on chromosomes 2q, 3p and 21q in Indian oral squamous cell carcinoma*, 48 BULL TOKYO DENT COLL. 109-117 (2007).

MFAP5 (MAGP2) encodes a multifunctional secreted protein that plays a role in elastic microfibril assembly, cell signaling, modulating endothelial cell behavior, and cell survival. See A. R. Albig et al., *Transcriptome analysis of endothelial cell gene expression induced by growth on matrigel matrices: identification and characterization of MAGP-2 and lumican as novel regulators of angiogenesis*, 10 ANGIOGENESIS 197-216 (2007); R. Lemaire et al., *Microfibril-associated MAGP-2 stimulates elastic fiber assembly*, 282 J BIOL CHEM. 800-808 (2007); K. A. Spivey et al., *A prognostic gene signature in advanced ovarian cancer reveals a microfibril-associated protein (MAGP2) as a promoter of tumor cell survival and angiogenesis*, 4 CELL ADH MIGR. (2010). Increased microvessel density associated with upregulation of MAGP2 suggests a role in tumor angiogenesis. See S. C. Mok et al., *A gene signature predictive for outcome in advanced ovarian cancer identifies a survival factor: microfibril-associated glycoprotein 2*, 16 CANCER CELL. 521-532 (2009). MFAP5 also demonstrated marked downregulation (FC=−44.48) in the study comparing differentially expressed genes in cutaneous squamous cell carcinoma versus normal skin. See S. H. Ra et al., *Molecular discrimination of cutaneous squamous cell carcinoma from actinic keratosis and normal skin*, MOD PATHOL (2011) (Advance online publication, Apr. 1, 2011). MFAP5 has also been shown to promote tumor and endothelial cell survival and endothelial cell motility in ovarian serous carcinomas. See S. C. Mok et al., *A gene signature predictive for outcome in advanced ovarian cancer identifies a survival factor: microfibril-associated glycoprotein 2*, 16 CANCER CELL. 521-532 (2009); K. A. Spivey et al., *A prognostic gene signature in advanced ovarian cancer reveals a microfibril-associated protein (MAGP2) as a promoter of tumor cell survival and angiogenesis*, 4 CELL ADH MIGR. (2010).

The downregulated genes CD36 and ZIC1 (FC=−2.77 and −2.48) have been described in association with tumorigenesis, but not with cutaneous squamous cell carcinoma. CD36 encodes a protein that serves as a receptor for thrombospondin in platelets and various cell lines. Because thrombospondins are widely distributed proteins involved in a variety of adhesive processes, this protein may have important functions as a cell adhesion molecule. It is known to bind to collagen, thrombospondin, anionic phospholipids, and oxidized LDL. See M. Chen et al., *Regulation of CD36 expression in human melanoma cells*, 507 ADV EXP MED BIOL. 337-342 (2002). The regulation of CD36 expression in tumor cells may play an important role in tumor growth, metastasis, and angiogenesis. The expression of CD36 and its downregulation has been described in melanoma cell lines. See M. Chen et al., *Regulation of CD36 expression in human melanoma cells*, 507 ADV EXP MED BIOL. 337-342 (2002); R. F. Thorne et al., *The integrins alpha3beta1 and alpha6beta1 physically and functionally associate with CD36 in human melanoma cells. Requirement for the extracellular domain OF CD36*, 275 J BIOL CHEM. 35264-35275 (2000). However, it has not been described in association with squamous cell carcinoma.

ZIC1 encodes a member of the ZIC family of C2H2-type zinc finger proteins that play important roles during development. Mutations in ZIC genes are associated with congenital anomalies such as holoprosencephaly, heterotaxy, and Dandy-Walker malformation. See J. Aruga et al., *Expression of ZIC family genes in meningiomas and other brain tumors*, 10 BMC CANCER 79 (2010). ZIC1 has been implicated in tumorigenesis, displaying downregulation through promoter hypermethylation in gastric cancer. See L. J. Wang et al., *ZIC1 is downregulated through promoter hypermethylation in gastric cancer*, 379 BIOCHEM BIOPHYS RES COMMUN. 959-963 (2009). ZIC1 has been shown to be upregulated in endometrial carcinoma, medulloblastoma, and meningiomas. See J. Aruga et al., *Expression of ZIC family genes in meningiomas and other brain tumors*, 10 BMC CANCER 79 (2010); E. M. Michiels et al., *Genes differentially expressed in medulloblastoma and fetal brain*, 1 PHYSIOL GENOMICS 83-91 (1999); Y. F. Wong et al., *Identification of molecular markers and signaling pathway in endometrial cancer in Hong Kong Chinese women by genome-wide gene expression profiling*, 26 ONCOGENE 1971-1982 (2007).

Both SNX21 and NPR3 were found to be downregulated (FC=−3.20 and −2.47). SNX21 encodes a member of the sorting nexin family that is involved in the regulation of receptor degradation and membrane trafficking and sorting within the cell. See C. A. Worby and J. E. Dixon, *Sorting out the cellular functions of sorting nexins*, 3 NAT REV MOL CELL BIOL. 919-931 (2002). NPR3 is part of a family of structurally-related but genetically-distinct hormones/paracrine factors that play a role in the regulation of blood volume, blood pressure, ventricular hypertrophy, pulmonary hypertension, fat metabolism, and long bone growth. See L. R. Potter et al., *Natriuretic peptides, their receptors, and cyclic guanosine monophosphate-dependent signaling functions*, 27 ENDOCR REV. 47-72 (2006). SNX21 and NPR3 have not been described in association with tumorigenesis and the significance of their downregulation in cutaneous SCC is unknown.

Pathways—Oxidative Phosphorylation/Mitochondrial Dysfunction

The oxidative phosphorylation and mitochondrial dysfunction signaling pathways were two of the most significantly enriched pathways among the 703 differentially expressed genes [−log(P-value)=14.6 and 10.2, respectively]. Mitochondria have many functions within the cells and are most known for the production of cellular energy in the form of ATP through oxidative phosphorylation. Mitochondria are also known to play important roles in apoptosis, cell proliferation, and in the modulation of calcium signaling. See S. Fulda et al., *Targeting mitochondria for cancer therapy*, 9 NAT REV DRUG DISCOV. 447-464 (2010); J. Lu et al., *Implications of mitochondrial DNA mutations and mitochondrial dysfunction in tumorigenesis*, 19 CELL RES. 802-815 (2009). Reprogramming of energy metabolism is one of the hallmarks of cancer. Normally, cells rely on mitochondrial oxidative phosphorylation to provide energy for cellular activities. Cancer cells are characterized by increased glycolysis and reduced mitochondrial respiratory function. Although many malignancies are known to demonstrate mitochondria dysfunction and alterations of oxidative phosphorylation, the exact mechanisms are unclear.

One of the postulated means of carcinogenesis includes generation of increased amounts of reactive oxygen radical species due to alterations of oxidative phosphorylation. Reactive oxygen radicals are known to provide a constant stimulus for cell proliferation and can cause further damage to both the nuclear and mitochondrial DNA. See J. S. Carew and P. Huang, *Mitochondrial defects in cancer*, 1 MOL CANCER 9 (2002). Another mechanism involves the loss of apoptosis regulation through mitochondrial pathways, which have been demonstrated in oral and head and neck squamous cell carcinoma cell lines. See C. C. Lin et al.,

*Berberine induces apoptosis in human HSC-3 oral cancer cells via simultaneous activation of the death receptor-mediated and mitochondrial pathway*, 27 ANTICANCER RES 3371-8 (2007); M. Zhao et al., *Head and neck cancer cell lines are resistant to mitochondrial-depolarization-induced apoptosis*, 70 ORL J OTORHINOLARYNGOL RELAT SPEC 257-63 (2008). Mitochondrial dysfunction is common in many types of cancers and has been reported in neoplasms of the breast, gastrointestinal tract, kidney, bladder, head and neck, prostate, and lung. See J. S. Carew and P. Huang, *Mitochondrial defects in cancer*, 1 MOL CANCER. 9 (2002). Although not previously described in the pathogenesis of cutaneous squamous cell carcinoma, alterations in mitochondrial function/oxidative phosphorylation may play a crucial role. Drugs targeting mitochondria are currently being investigated and present a promising avenue for further research. See S. Fulda et al., *Targeting mitochondria for cancer therapy*, 9 NAT REV DRUG DISCOV. 447-464 (2010).

Pathways—Polyamine Regulation in Colon Cancer

The polyamine regulation pathways was another significantly altered pathway [−log(P-value)=10.5]. Polyamines are a group of aliphatic biogenic amines including putrescine, spermidine, and spermine. An important step in their biosynthesis involves the decarboxylation of ornithine by ornithine decarboxylase to produce putrescine which provides the precursor to spermidine and spermine. See S. K. Gilmour, *Polyamines and nonmelanoma skin cancer*, 224 TOXICOL APPL PHARMACOL. 249-256 (2007). Polyamines are known to known to have many roles within the cell including support of growth, maintenance of chromatin conformation, regulation of specific gene expression, ion-channel regulation, maintenance of membrane stability, provision of a precursor in the synthesis of eukaryotic translation initiation factor 5A (IF5A), and free-radical scavenging. See R. A. Casero et al., *Targeting polyamine metabolism and function in cancer and other hyperproliferative diseases*, 6 NAT REV DRUG DISCOV. 373-390 (2007). Aberrations of polyamine metabolism has been identified most notably in prostate carcinoma (see N. Palavan-Unsal et al., *The function of poliamine metabolism in prostate cancer*, 28 EXP ONCOL. 178-186 (2006)), colon carcinoma (see L. J. Wang et al., *Z1C1 is downregulated through promoter hypermethylation in gastric cancer*, 379 BIOCHEM BIOPHYS RES COMMUN. 959-963 (2009)), and nonmelanoma skin carcinoma.

Increased polyamines and ornithine decarboxylase activity have been associated with skin tumorigenesis and their levels have been found elevated in human non-melanoma skin carcinomas. See C. A. Elmets and M. Athar, *Targeting ornithine decarboxylase for the prevention of nonmelanoma skin cancer in humans*, 3 CANCER PREV RES (PHILA). 8-11 (2010). Murine models have demonstrated that elevated levels of polyamines have a causal role in skin tumor development. See S. K. Gilmour, *Polyamines and nonmelanoma skin cancer*, 224 TOXICOL APPL PHARMACOL. 249-256 (2007). In addition, these animal models have demonstrated the suppression of skin carcinomas with oral and topical inhibitors of polyamine synthesis. Alpha-difluromethylornithine, an irreversible inhibitor of ornithine decarboxylase, has been shown to reduce the tissue levels of polyamines in human skin. See D. S. Alberts et al., *Chemoprevention of human actinic keratoses by topical 2-(difluoromethyl)-dl-ornithine*, 9 CANCER EPIDEMIOL BIOMARKERS PREV. 1281-1286 (2000); H. H. Bailey et al., *A randomized, double-blind, placebo-controlled phase 3 skin cancer prevention study of {alpha}-difluoromethylornithine in subjects with previous history of skin cancer*, 3 CANCER PREV RES (PHILA). 35-47 (2010). A randomized, double blinded, placebo controlled phase 3 skin cancer prevention study utilizing oral alpha-difluoromethylornithine in patients with a previous history of skin cancer revealed significant reductions in new basal cell carcinomas. See H. H. Bailey et al., *A randomized, double-blind, placebo-controlled phase 3 skin cancer prevention study of {alpha}-difluoromethylomithine in subjects with previous history of skin cancer*, 3 CANCER PREV RES (PHILA). 35-47 (2010). Another randomized, placebo-controlled Phase IIb study using topical alpha-difluoromethylornithine demonstrated a significant reduction in pre-existing actinic keratoses. See D. S. Alberts et al., *Chemoprevention of human actinic keratoses by topical 2-(difluoromethyl)-dl-ornithine*, 9 CANCER EPIDEMIOL BIOMARKERS PREV. 1281-1286 (2000). More work into inhibiting this pathway may provide a chemotherapeutic agent effective in treating non-melanoma skin carcinomas.

Pathways—Protein Ubiquitination Pathway

The protein ubiquitination pathway was also significant in the pathway analysis [−log(P-value)=8.8]. Ubiquitin is a molecular marker that identifies proteins for either degradation through a proteasome dependent pathway or signaling or trafficking events through a proteasome independent pathway. The proteins regulated by ubiquitination control numerous cellular processes including cell proliferation, signal transduction, apoptosis, transcriptional regulation, receptor modulation and endocytosis. See S. R. Ande et al., *The ubiquitin pathway: an emerging drug target in cancer therapy*, 625 EUR J PHARMACOL. 199-205 (2009); D. Hoeller and I. Dikic, *Targeting the ubiquitin system in cancer therapy*, 458 NATURE 438-444 (2009). One of the mechanisms of carcinogenesis is through alterations of ubiquitin-dependent degradation of regulatory proteins including tumor suppressors and abnormal stabilization of oncogenic proteins. See S. Y. Fuchs, *De-regulation of ubiquitin-dependent proteolysis and the pathogenesis of malignant melanoma*, 24 CANCER METASTASIS REV. 329-338 (2005).

Deregulation of the ubiquitin pathway has been implicated in carcinomas from the lung, stomach, colon, and rectum and in lymphoproliferative disorders. See D. Hoeller et al., *Ubiquitin and ubiquitin-like proteins in cancer pathogenesis*, 6 NAT REV CANCER 776-788 (2006). Aberrations within the ubiquitin pathway have been described in skin malignancies including squamous cell carcinoma, basal cell carcinoma, and melanoma. See S. Y. Fuchs, *De-regulation of ubiquitin-dependent proteolysis and the pathogenesis of malignant melanoma*, 24 CANCER METASTASIS REV. 329-338 (2005); K. Nakayama, *Growth and progression of melanoma and non-melanoma skin cancers regulated by ubiquitination*, 23 PIGMENT CELL MELANOMA RES. 338-351 (2010). The protein ubiquitination pathway involves a complex network of proteins including E3 ubiquitin ligases, deubiquitinases, protesomes, and E1 activating enzymes that have already been targeted in cancer therapy. See S. R. Ande et al., *The ubiquitin pathway: an emerging drug target in cancer therapy*, 625 EUR J PHARMACOL. 199-205 (2009); D. Hoeller and I. Dikic, *Targeting the ubiquitin system in cancer therapy*, 458 NATURE 438-444 (2009); D. Hoeller et al., *Ubiquitin and ubiquitin-like proteins in cancer pathogenesis*, 6 NAT REV CANCER 776-788 (2006). Bortezomib is an anticancer drug that targets the proteasome and has been approved for the treatment of patients with multiple myeloma and mantle cell lymphoma. See D. Hoeller et al., *Ubiquitin and ubiquitin-like proteins in cancer pathogenesis*, 6 NAT REV CANCER 776-788 (2006). Many drugs targeting proteasomes and other proteins within the ubiquitination pathway are currently under investigation with several promising clinical trials underway. See D. Hoeller and I.

Dikic, *Targeting the ubiquitin system in cancer therapy*, 458 NATURE 438-444 (2009); D. Hoeller et al., *Ubiquitin and ubiquitin-like proteins in cancer pathogenesis*, 6 NAT REV CANCER 776-788 (2006).

Several genes in the microarray study (upregulated genes S100A8, S100A9, MMP1 and the downregulated gene MFAP5) overlapped with a previous DNA microarray study comparing squamous cell carcinoma versus normal skin. See S. H. Ra et al., *Molecular discrimination of cutaneous squamous cell carcinoma from actinic keratosis and normal skin*, MOD PATHOL (2011) (Advance online publication, Apr. 1, 2011). None of the enriched molecular pathways in the study were identified as significantly enriched in the previous study. However, all of these pathways have been described in association with malignancy.

Example 2: Identification of Squamous Cell Carcinoma

Total RNA is isolated from a formalin-fixed, paraffin-embedded tissue sample from a human. Multiplex PCR is performed using KRT9 and C15orf48 Taqman probe/primers and 1 µg of total RNA (PCR Machine being the *Applied Biosystems* 7500 Fast Real-Time PCR System). The CT value for C15orf48 is lower than the CT value for KRT9, indicating the sample is squamous cell carcinoma.

Example 3: Identification of Pseudoepitheliomatous Hyperplasia

Total RNA is isolated from a formalin-fixed, paraffin-embedded tissue sample from a human. Multiplex PCR is performed using KRT9 and C15orf48 Taqman probe/primers and 1 µg of total RNA (PCR Machine being the *Applied Biosystems* 7500 Fast Real-Time PCR System). The CT value for C15orf48 is higher than the CT value for KRT9, indicating the sample is pseudoepitheliomatous hyperplasia.

A method for differentiating cutaneous squamous cell carcinoma from pseudoepitheliomatous hyperplasia in a biological sample, which may be from a human, comprising:
(a) isolating total RNA from said sample;
(b) performing multiplex PCR using KRT9 and C15orf48 probes/primers and said isolated RNA;
(c) obtaining a CT value for KRT9; and
(d) obtaining a CT value for C15orf48,
wherein said sample is cutaneous squamous cell carcinoma if the CT value of C15orf48 is lower than the CT value of KRT9, and
wherein said sample is pseudoepitheliomatous hyperplasia if the CT value of C15orf48 is higher than the CT value of KRT9.

A diagnostic kit for assaying a biological sample, said kit comprising an agent for detecting KRT9, an agent for detecting C15orf48, one or more reagents useful for facilitating said detection, and instructions for use of said kit.

A method for differentiating cutaneous squamous cell carcinoma from pseudoepitheliomatous hyperplasia comprising obtaining a sample to be assayed and performing gene expression microarray analysis on said sample.

Said gene expression microarray may measure the levels of KRT9 and C15orf48 mRNA by Real-Time PCR.

Cutaneous squamous cell carcinoma may be identified when, by measuring the levels of KRT9 and C15orf48, the CT value obtained for C15orf48 is lower than the CT value obtained for KRT9.

Pseudoepitheliomatous hyperplasia may be identified when, by measuring the levels of KRT9 and C15orf48, the CT value obtained for C15orf48 is higher than the CT value obtained for KRT9.

A method of using differentially expressed genes as prognostic markers for cutaneous squamous cell carcinoma.

A method of using molecular pathways as targets for the treatment of cutaneous squamous cell carcinoma.

The molecular pathway may be chosen from a list consisting of oxidative phosphorylation, polyamine regulation in colon cancer, mitochondrial dysfunction, and protein ubiquitination.

A method for identifying squamous cell carcinoma in a biological sample comprising:
(a) obtaining said biological sample;
(b) isolating total RNA from said sample;
(c) performing multiplex PCR using KRT9 and C15orf48 probes/primers and said isolated RNA;
(d) obtaining a CT value for KRT9;
(e) obtaining a CT value for C15orf48; and
(f) using said CT values to identify squamous cell carcinoma,
wherein the CT value of C15orf48 is lower than the CT value of KRT9.

A method for identifying pseudoepitheliomatous hyperplasia in a biological sample, which may be from a human, comprising:
(a) obtaining said biological sample;
(b) isolating total RNA from said sample;
(c) performing multiplex PCR using KRT9 and C15orf48 probes/primers and said isolated RNA;
(d) obtaining a CT value for KRT9;
(e) obtaining a CT value for C15orf48; and
(f) using said CT values to identify squamous cell carcinoma,
wherein the CT value of C15orf48 is higher than the CT value of KRT9.

A method for differentiating squamous cell carcinoma from pseudoepitheliomatous hyperplasia in a biological sample, which may be from a human, comprising:
(a) isolating total RNA from said sample;
(b) performing multiplex PCR using KRT9 and C15orf48 probes/primers and said isolated RNA;
(c) obtaining a CT value for KRT9; and
(d) obtaining a CT value for C15orf48,
wherein said sample is squamous cell carcinoma if the CT value of C15orf48 is lower than the CT value of KRT9, and
wherein said sample is pseudoepitheliomatous hyperplasia if the CT value of C15orf48 is higher than the CT value of KRT9.

All publications cited herein, including the following, are expressly incorporated herein by reference in their entireties for all purposes.

REFERENCES

1. Alam M, Ratner D. Cutaneous squamous cell carcinoma. *N Eng J Med* 2001; 344: 975-83.
2. Smoller B R. Squamous cell carcinoma: from precursor lesions to high-risk variants. *Mod Pathol* 2006; 19 Suppl 2(S88-92).
3. Grunwald M H, Lee J Y, Ackerman A B. Pseudocarcinomatous hyperplasia. *Am J Dermatopathol* 1988; 10: 95-103.
4. Zayour M, Lazova R. Pseudoepitheliomatous hyperplasia: a review. *Am J Dermatopathol* 2011; 33: 112-22.

5. Kluger N, Durand L, Minier-Thoumin C, et al. Pseudoepitheliomatous epidermal hyperplasia in tattoos: a report of three cases. *Am J Clin Dermatol* 2008; 9: 337-40.
6. Dooley T P, Reddy S P, Wilborn T W, et al. Biomarkers of human cutaneous squamous cell carcinoma from tissues and cell lines identified by DNA microarrays and qRT-PCR. *Biochem Biophys Res Commun* 2003; 11: 1026-36.
7. Haider A S, Peters S B, Kaporis H, et al. Genomic analysis defines a cancer-specific gene expression signature for human squamous cell carcinoma and distinguishes malignant hyperproliferation from benign hyperplasia. *J Invest Dermatol* 2006; 126: 869-81.
8. Kathpalia V P, Mussak E N, Chow S S, et al. Genome-wide transcriptional profiling in human squamous cell carcinoma of the skin identifies unique tumor-associated signatures. *J Dermatol* 2006; 33: 309-18.
9. Nindl I, Dang C, Forschner T, et al. Identification of differentially expressed genes in cutaneous squamous cell carcinoma by microarray expression profiling. *Mol Cancer* 2006; 5: 30.
10. Ra S H, Li X M, Binder S. Molecular discrimination of cutaneous squamous cell carcinoma from actinic keratosis and normal skin. *Mod Pathol* 2011; Advance online publication, Apr. 1, 2011.
11. Emberley E D, Murphy L C, Watson P H. S100 proteins and their influence on pro-survival pathways in cancer. *Biochem Cell Biol* 2004; 82: 508-15.
12. Moubayed N, Weichenthal M, Harder J, Wandel E, Sticherling M, Glaser R. Psoriasin (S100A7) is significantly up-regulated in human epithelial skin tumours. *J Cancer Res Clin Oncol* 2007; 133: 253-61.
13. Alowami S, Qing G, Emberley E, Snell L, Watson P H. Psoriasin (S100A7) expression is altered during skin tumorigenesis. *BMC Dermatol* 2003; 3: 1.
14. Salama I, Malone P S, Mihaimeed F, Jones J L. A review of the S100 proteins in cancer. *Eur J Surg Oncol* 2008; 34: 357-64.
15. Oikonomopoulou K, Diamandis E P, Hollenberg M D. Kallikrein-related peptidases: proteolysis and signaling in cancer, the new frontier. *Biol Chem* 2010; 391: 299-310.
16. Naidoo S, Raidoo D M. Angiogenesis in cervical cancer is mediated by HeLa metabolites through endothelial cell tissue kallikrein. *Oncol Rep* 2009; 22: 285-93.
17. Rückert F, Hennig M, Petraki C D, et al. Co-expression of KLK6 and KLK10 as prognostic factors for survival in pancreatic ductal adenocarcinoma. *Br J Cancer* 2008; 99: 1484-92.
18. Klucky B, Mueller R, Vogt I, et al. Kallikrein 6 induces E-cadherin shedding and promotes cell proliferation, migration, and invasion. *Cancer Res* 2007; 67: 8198-206.
19. Kountourakis P, Psyrri A, Scorilas A, et al. Prognostic value of kallikrein-related peptidase 6 protein expression levels in advanced ovarian cancer evaluated by automated quantitative analysis (AQUA). *Cancer Sci* 2008; 99: 2224-9.
20. Nagahara H, Mimori K, Utsunomiya T, et al. Clinicopathologic and biological significance of kallikrein 6 overexpression in human gastric cancer. *Clin Cancer Res* 2005; 11(19 Pt 1): 6800-6.
21. Ogawa K, Utsunomiya T, Mimori K, et al. Clinical significance of human kallikrein gene 6 messenger RNA expression in colorectal cancer. *Clin Cancer Res* 2005; 11: 2889-93.
22. Anisowicz A, Sotiropoulou G, Stenman G, Mok S C, Sager R. A novel protease homolog differentially expressed in breast and ovarian cancer. *Mol Med* 1996; 2: 624-36.
23. Henkhaus R S, Gerner E W, Ignatenko N A. Kallikrein 6 is a mediator of K-RAS-dependent migration of colon carcinoma cells. *Biol Chem* 2008; 389: 757-64.
24. Santin A D, Diamandis E P, Bellone S, et al. Human kallikrein 6: a new potential serum biomarker for uterine serous papillary cancer. *Clin Cancer Res* 2005; 11: 3320-5.
25. Dorman G, Cseh S, Hajdú I, et al. Matrix metalloproteinase inhibitors: a critical appraisal of design principles and proposed therapeutic utility. *Drugs* 2010; 70: 949-64.
26. Folgueras A R, Pendás A M, Sánchez L M, et al. Matrix metalloproteinases in cancer: from new functions to improved inhibition strategies. *Int J Dev Biol* 2004; 48: 411-24.
27. Freije J M, Balbin M, Pendás A M, et al. Matrix metalloproteinases and tumor progression. *Adv Exp Med Biol* 2003; 532: 91-107.
28. Saleh A, Zain R B, Hussaini H, et al. Transcriptional profiling of oral squamous cell carcinoma using formalin-fixed paraffin-embedded samples. *Oral Oncol* 2010; 46: 379-86.
29. Stokes A, Joutsa J, Ala-Aho R, et al. Expression profiles and clinical correlations of degradome components in the tumor microenvironment of head and neck squamous cell carcinoma. *Clin Cancer Res* 2010; 16: 2022-35.
30. Suhr M L, Dysvik B, Bruland O, et al. Gene expression profile of oral squamous cell carcinomas from Sri Lankan betel quid users. *Oncol Rep* 2007; 18: 1061-75.
31. Toruner G A, Ulger C, Alkan M, et al. Association between gene expression profile and tumor invasion in oral squamous cell carcinoma. *Cancer Genet Cytogenet* 2004; 154: 27-35.
32. Soya P, Feng Q, Geiss G, et al. Discovery of novel methylation biomarkers in cervical carcinoma by global demethylation and microarray analysis. *Cancer Epidemiol Biomarkers Prev* 2006; 15: 114-23.
33. Zhou J, Wang H, Lu A, et al. A novel gene, NMES1, downregulated in human esophageal squamous cell carcinoma. *Int J Cancer* 2002; 101: 311-6.
34. Razmara M, Srinivasula S M, Wang L, et al. CARD-8 protein, a new CARD family member that regulates caspase-1 activation and apoptosis. *J Biol Chem* 2002; 277: 13952-8.
35. Pinto do O P, Richter K, Carlsson L. Hematopoietic progenitor/stem cells immortalized by Lhx2 generate functional hematopoietic cells in vivo. *Blood* 2002; 99: 3939-46.
36. Wu H K, Heng H H, Siderovski D P, et al. Identification of a human LIM-Hox gene, hLH-2, aberrantly expressed in chronic myelogenous leukaemia and located on 9q33-34.1. *Oncogene* 1996; 12: 1205-12.
37. Bloor B K, Tidman N, Leigh I M, et al. Expression of keratin K2e in cutaneous and oral lesions: association with keratinocyte activation, proliferation, and keratinization. *Am J Pathol* 2003; 162: 963-75.
38. Rothnagel J A, Traupe H, Wojcik S, et al. Mutations in the rod domain of keratin 2e in patients with ichthyosis bullosa of Siemens. *Nat Genet* 1994; 7: 485-90.
39. Reis A, Hennies H C, Langbein L, et al. Keratin 9 gene mutations in epidermolytic palmoplantar keratoderma (EPPK). *Nat Genet* 1994; 6: 174-9.
40. Bodey B, Bodey B Jr, Gröger A M, Siegel S E, Kaiser H E. Immunocytochemical detection of homeobox B3, B4, and C6 gene product expression in lung carcinomas. *Anticancer Res* 2000; 20: 2711-6.
41. McCabe C D, Spyropoulos D D, Martin D, Moreno C S. Genome-wide analysis of the homeobox C6 transcriptional network in prostate cancer. *Cancer Res* 2008; 68: 1988-96.
42. Chen K N, Gu Z D, Ke Y, Li J Y, Shi X T, Xu G W. Expression of 11 HOX genes is deregulated in esophageal squamous cell carcinoma. *Clin Cancer Res* 2005; 11: 1044-9.
43. Miller G J, Miller H L, van Bokhoven A, et al. Aberrant HOXC expression accompanies the malignant phenotype in human prostate. *Cancer Res* 2003; 63: 5879-88.
44. Bodey B, Bodey B Jr, Siegel S E, Kaiser H E. Immunocytochemical detection of the homeobox B3, B4, and C6 gene products in breast carcinomas. *Anticancer Res* 2000; 20: 3281-6.
45. Haase V H. The VHL tumor suppressor: master regulator of HIF. *Curr Pharm Des* 2009; 15: 3895-903.
46. Kaelin W G Jr. Treatment of kidney cancer: insights provided by the VHL tumor-suppressor protein. *Cancer* 2009; 115: 2262-72.
47. Stephen J K, Chen K M, Raitanen M, Grénman S, Worsham M J. DNA hypermethylation profiles in squamous cell carcinoma of the vulva. *Int J Gynecol Pathol* 2009; 28: 63-75.
48. Asakawa T, Esumi M, Endo S, Kida A, Ikeda M. Tongue cancer patients have a high frequency of allelic loss at the von Hippel-Lindau gene and other loci on 3p. *Cancer* 2008; 112: 527-34.
49. Yamamoto N, Kuroiwa T, Katakura A, Shibahara T, Choudhury C. Loss of heterozygosity (LOH) on chromosomes 2q, 3p and 21q in Indian oral squamous cell carcinoma. *Bull Tokyo Dent Coll* 2007; 48: 109-17.
50. Choi C H, Lee K M, Choi J J, et al. Hypermethylation and loss of heterozygosity of tumor suppressor genes on chromosome 3p in cervical cancer. *Cancer Lett* 2007; 255: 26-33.
51. Albig A R, Roy T G, Becenti D J, Schiemann W P. Transcriptome analysis of endothelial cell gene expression induced by growth on matrigel matrices: identification and characterization of MAGP-2 and lumican as novel regulators of angiogenesis. *Angiogenesis* 2007; 10: 197-216.
52. Lemaire R, Bayle J, Mecham R P, Lafyatis R. Microfibril-associated MAGP-2 stimulates elastic fiber assembly. *J Biol Chem* 2007; 282: 800-8.
53. Spivey K A, Banyard J. A prognostic gene signature in advanced ovarian cancer reveals a microfibril-associated protein (MAGP2) as a promoter of tumor cell survival and angiogenesis. *Cell Adh Migr* 2010; 4.
54. Mok S C, Bonome T, Vathipadiekal V, et al. A gene signature predictive for outcome in advanced ovarian cancer identifies a survival factor: microfibril-associated glycoprotein 2. *Cancer Cell* 2009; 16: 521-32.
55. Thorne R F, Marshall J F, Shafren D R, Gibson P G, Hart I R, Burns G F. The integrins alpha3beta1 and alpha6beta1 physically and functionally associate with CD36 in human melanoma cells. Requirement for the extracellular domain OF CD36. *J Biol Chem* 2000; 275: 35264-75.
56. Chen M, Pych E, Corpron C, Harmon C M. Regulation of CD36 expression in human melanoma cells. *Adv Exp Med Biol* 2002; 507: 337-42.
57. Aruga J, Nozaki Y, Hatayama M, Odaka Y S, Yokota N. Expression of ZIC family genes in meningiomas and other brain tumors. *BMC Cancer* 2010; 10: 79.
58. Wang L J, Jin H C, Wang X, et al. ZIC1 is downregulated through promoter hypermethylation in gastric cancer. *Biochem Biophys Res Commun* 2009; 379: 959-63.
59. Wong Y F, Cheung T H, Lo K W, et al. Identification of molecular markers and signaling pathway in endometrial cancer in Hong Kong Chinese women by genome-wide gene expression profiling. *Oncogene* 2007; 26: 1971-82.
60. Michiels E M, Oussoren E, Van Groenigen M, et al. Genes differentially expressed in medulloblastoma and fetal brain. *Physiol Genomics* 1999; 1: 83-91.
61. Worby C A, Dixon J E. Sorting out the cellular functions of sorting nexins. *Nat Rev Mol Cell Biol* 2002; 3: 919-31.
62. Potter L R, Abbey-Hosch S, Dickey D M. Natriuretic peptides, their receptors, and cyclic guanosine monophosphate-dependent signaling functions. *Endocr Rev* 2006; 27: 47-72.
63. Lu J, Sharma L K, Bai Y. Implications of mitochondrial DNA mutations and mitochondrial dysfunction in tumorigenesis. *Cell Res* 2009; 19: 802-15.
64. Fulda S, Galluzzi L, Kroemer G. Targeting mitochondria for cancer therapy. *Nat Rev Drug Discov* 2010; 9: 447-64.
65. Carew J S, Huang P. Mitochondrial defects in cancer. *Mol Cancer* 2002; 1: 9.
66. Lin C C, Yang J S, Chen J T, et al. Berberine induces apoptosis in human HSC-3 oral cancer cells via simultaneous activation of the death receptor-mediated and mitochondrial pathway. *Anticancer Res* 2007; 27: 3371-8.
67. Zhao M, Mydlarz W K, Zhou S, Califano J. Head and neck cancer cell lines are resistant to mitochondrial-depolarization-induced apoptosis. *ORL J Otorhinolaryngol Relat Spec* 2008; 70: 257-63.
68. Gilmour S K. Polyamines and nonmelanoma skin cancer. *Toxicol Appl Pharmacol* 2007; 224: 249-56.
69. Casero R A Jr, Marton L J. Targeting polyamine metabolism and function in cancer and other hyperproliferative diseases. *Nat Rev Drug Discov* 2007; 6: 373-90.
70. Elmets C A, Athar M. Targeting ornithine decarboxylase for the prevention of nonmelanoma skin cancer in humans. *Cancer Prev Res (Phila)* 2010; 3: 8-11.
71. Palavan-Unsal N, Aloglu-Senturk S M, Arsan D. The function of poliamine metabolism in prostate cancer. *Exp Oncol* 2006; 28: 178-86.
72. Wallace H M, Caslake R. Polyamines and colon cancer. *Eur J Gastroenterol Hepatol* 2001; 13: 1033-9.
73. Bailey H H, Kim K, Verma A K, et al. A randomized, double-blind, placebo-controlled phase 3 skin cancer prevention study of {alpha}-difluoromethylornithine in subjects with previous history of skin cancer. *Cancer Prev Res (Phila)* 2010; 3: 35-47.
74. Alberts D S, Dorr R T, Einspahr J G, et al. Chemoprevention of human actinic keratoses by topical 2-(difluoromethyl)-dl-ornithine. *Cancer Epidemiol Biomarkers Prev* 2000; 9: 1281-6.
75. Ande S R, Chen J, Maddika S. The ubiquitin pathway: an emerging drug target in cancer therapy. *Eur J Pharmacol* 2009; 625: 199-205.
76. Hoeller D, Dikic I. Targeting the ubiquitin system in cancer therapy. *Nature* 2009; 458: 438-44.
77. Fuchs S Y. De-regulation of ubiquitin-dependent proteolysis and the pathogenesis of malignant melanoma. *Cancer Metastasis Rev* 2005; 24: 329-38.
78. Hoeller D, Hecker C M, Dikic I. Ubiquitin and ubiquitin-like proteins in cancer pathogenesis. *Nat Rev Cancer* 2006; 6: 776-88.
79. Nakayama K. Growth and progression of melanoma and non-melanoma skin cancers regulated by ubiquitination. *Pigment Cell Melanoma Res* 2010; 23: 338-51.

What is claimed is:

1. A diagnostic kit for assaying a biological sample, said kit comprising a first fluorescently labeled nucleic acid probe for KRT9 (keratin 9), a second fluorescently labeled nucleic acid probe for C15orf48 (chromosome 15 open reading frame 48), and instructions for use of said kit.

2. The diagnostic kit according to claim 1, wherein the first and second fluorescently labeled nucleic acid probes are hydrolysis probes for real-time polymerase chain reactions.

3. The diagnostic kit according to claim 2, wherein the hydrolysis probes comprise an oligonucleotide probe having a fluorophore attached to the 5'-end and a quencher attached at the 3'-end.

4. The diagnostic kit according to claim 1, and further comprising a primer pair for KRT9.

5. The diagnostic kit according to claim 4, wherein the primers are: GCCTGCTTATTGGATCCTGA (SEQ ID NO: 9) and CAGGCCAGAGAGAGGAAAGA (SEQ ID NO: 10).

6. The diagnostic kit according to claim 1, and further comprising a primer pair for C15orf48.

7. The diagnostic kit according to claim 6, wherein the primers are: AAGGGTGACCAAATGACGAG (SEQ ID NO: 7) and TGCAGTTATTGCTGCACTCC (SEQ ID NO: 8).

8. A diagnostic kit for assaying a biological sample, said kit comprising a first fluorescently labeled nucleic acid probe for KRT9, a second fluorescently labeled nucleic acid probe for detecting C15orf48, a first primer pair for KRT9, a second primer pair for C15orf48, and instructions for use of said kit.

9. The diagnostic kit according to claim 8, wherein the first and second fluorescently labeled nucleic acid probes are hydrolysis probes for real-time polymerase chain reactions.

10. The diagnostic kit according to claim 9, wherein the hydrolysis probes comprise an oligonucleotide probe having a fluorophore attached to the 5'-end and a quencher attached at the 3'-end.

11. The diagnostic kit according to claim 8, wherein the primers of the first primer pair are: GCCTGCTTATTGGATCCTGA (SEQ ID NO: 9) and CAGGCCAGAGAGAGGAAAGA (SEQ ID NO: 10).

12. The diagnostic kit according to claim 8, wherein the primers of the second primer pair are: AAGGGTGACCAAATGACGAG (SEQ ID NO: 7) and TGCAGTTATTGCTGCACTCC (SEQ ID NO: 8).

13. A method for determining the relative expression levels of both KRT9 and C15orf48 in cells of a cutaneous squamous lesion, which comprises
  (a) isolating total RNA from the cells;
  (b) performing multiplex PCR using the kit according to claim 1 and the isolated RNA to obtain a CT value for KRT9 and a CT value for C15orf48; and
  (c) determining whether the expression level of C15orf48 is more or less than that of KRT9.

14. The method according to claim 13, wherein said cutaneous squamous lesion is obtained from a human.

* * * * *